(12) United States Patent
Christoffersen et al.

(10) Patent No.: US 7,614,545 B2
(45) Date of Patent: Nov. 10, 2009

(54) ELECTRONIC MARKING OF A MEDICATION CARTRIDGE

(75) Inventors: Lasse Wengel Christoffersen, Soborg (DK); Preben Mikael Nielsen, Holbaek (DK); Bo Erik Lennart Berggren, Lund (SE)

(73) Assignee: Novo Nordisk A/S, Bagsvaerd (DK)

(*) Notice: Subject to any disclaimer, the term of this patent is extended or adjusted under 35 U.S.C. 154(b) by 0 days.

(21) Appl. No.: 11/232,469

(22) Filed: Sep. 19, 2005

(65) Prior Publication Data

US 2006/0118612 A1 Jun. 8, 2006

Related U.S. Application Data

(63) Continuation of application No. PCT/DK2004/000199, filed on Mar. 23, 2004.

(30) Foreign Application Priority Data

Mar. 24, 2003 (DK) .......................... PA 2003 00448

(51) Int. Cl.
```
G06K 19/00      (2006.01)
G06K 19/06      (2006.01)
G06K 7/10       (2006.01)
G06K 7/08       (2006.01)
```
(52) U.S. Cl. .................. 235/375; 235/462.01; 235/487; 235/494; 235/492; 235/451
(58) Field of Classification Search ................ 235/487, 235/492, 494, 451, 462.01; 283/83; 341/16; 604/404
See application file for complete search history.

(56) References Cited

U.S. PATENT DOCUMENTS

| | | | |
|---|---|---|---|
| 3,700,862 A | 10/1972 | Snook et al. | |
| 3,809,863 A | 5/1974 | Oberg | |
| 3,916,157 A | 10/1975 | Roulette et al. | |
| 4,179,212 A * | 12/1979 | Lahr | ............................ 399/79 |
| 4,327,283 A | 4/1982 | Henman et al. | |
| 4,355,300 A * | 10/1982 | Weber | ......................... 235/451 |
| 4,420,754 A | 12/1983 | Andermo | |

(Continued)

FOREIGN PATENT DOCUMENTS

DE        3712089        10/1988

(Continued)

OTHER PUBLICATIONS

English language abstract of JP 09-034361.

(Continued)

*Primary Examiner*—Daniel Walsh
(74) *Attorney, Agent, or Firm*—Welsey A. Nicolas; Reza Green; Marc A. Began

(57) ABSTRACT

The invention relates to a marking of cartridges, carpules or any kind of package. The marking can be in an electronically readable form while being transparent. Hereby a marking with improved security for avoiding reading errors which ensures a mandatory visual inspection of content is obtained. The transparent conductor can be in form of a polymer, an ITO and the like. These transparent conductors are used in an improved marking technique, which further improves reading security. The invention may e.g. be used in connection with medication delivery devices for self-treatment of a disease, e.g. diabetes.

26 Claims, 22 Drawing Sheets

U.S. PATENT DOCUMENTS

| | | | |
|---|---|---|---|
| 4,449,042 A | 5/1984 | Hampson et al. | |
| 4,476,149 A | 10/1984 | Poppe et al. | |
| 4,476,381 A | 10/1984 | Rubin | |
| 4,591,707 A * | 5/1986 | Stenzel et al. | 283/83 |
| 4,625,101 A | 11/1986 | Hinks et al. | |
| 4,693,574 A | 9/1987 | Ohnuki et al. | |
| 4,731,526 A | 3/1988 | Knoll et al. | |
| 4,739,377 A | 4/1988 | Allen | |
| 4,810,867 A | 3/1989 | Speicher | |
| 4,850,966 A | 7/1989 | Grau et al. | |
| 4,853,521 A | 8/1989 | Claeys et al. | |
| 4,857,716 A | 8/1989 | Gombrich et al. | |
| 4,930,263 A | 6/1990 | Rando | |
| 4,959,056 A * | 9/1990 | Dombrowski et al. | 604/186 |
| 4,978,335 A * | 12/1990 | Arthur, III | 604/67 |
| 5,059,776 A | 10/1991 | Antes | |
| 5,078,683 A | 1/1992 | Sancoff et al. | |
| 5,091,798 A | 2/1992 | Hibino | |
| 5,132,026 A | 7/1992 | Baluyet et al. | |
| 5,153,827 A | 10/1992 | Courte et al. | |
| 5,196,683 A | 3/1993 | Marom et al. | |
| 5,305,147 A | 4/1994 | Hasegawa et al. | |
| 5,311,364 A | 5/1994 | Kanoshima et al. | |
| 5,317,506 A | 5/1994 | Coutre et al. | |
| 5,336,871 A | 8/1994 | Colgate, Jr. | |
| 5,379,131 A | 1/1995 | Yamazaki | |
| 5,394,206 A | 2/1995 | Cocca | |
| 5,403,616 A * | 4/1995 | Hattori et al. | 427/126.3 |
| 5,418,649 A | 5/1995 | Igarashi | |
| 5,422,472 A | 6/1995 | Tavislan et al. | |
| 5,430,278 A * | 7/1995 | Krieg et al. | 235/449 |
| 5,432,329 A | 7/1995 | O'Boyle et al. | |
| 5,461,239 A | 10/1995 | Atherton | |
| 5,523,560 A | 6/1996 | Manique et al. | |
| 5,569,212 A * | 10/1996 | Brown | 604/207 |
| 5,585,615 A | 12/1996 | Iwanami et al. | |
| 5,628,309 A * | 5/1997 | Brown | 600/310 |
| 5,637,854 A * | 6/1997 | Thomas | 235/462.14 |
| 5,643,212 A | 7/1997 | Coutre et al. | |
| 5,675,380 A | 10/1997 | Florent | |
| 5,686,725 A * | 11/1997 | Maruyama et al. | 250/271 |
| 5,747,350 A | 5/1998 | Sattler | |
| 5,757,521 A * | 5/1998 | Walters et al. | 359/2 |
| 5,786,584 A | 7/1998 | Button et al. | |
| 5,792,117 A * | 8/1998 | Brown | 604/207 |
| 5,793,502 A | 8/1998 | Bianco | |
| 5,821,524 A | 10/1998 | Horlbeck | |
| 5,882,463 A | 3/1999 | Tompkin et al. | |
| 5,895,369 A | 4/1999 | Flower | |
| 5,902,990 A * | 5/1999 | Stewart | 235/483 |
| 5,954,700 A * | 9/1999 | Kovelman | 604/232 |
| 6,003,775 A | 12/1999 | Ackley | |
| 6,019,745 A | 2/2000 | Gray | |
| 6,047,892 A | 4/2000 | Schuessler et al. | |
| 6,053,415 A | 4/2000 | Norwood | |
| 6,090,064 A * | 7/2000 | Reilly et al. | 604/506 |
| 6,110,152 A * | 8/2000 | Kovelman | 604/232 |
| 6,168,080 B1 * | 1/2001 | Verschuur et al. | 235/462.01 |
| 6,177,683 B1 * | 1/2001 | Kolesar et al. | 250/566 |
| 6,202,929 B1 * | 3/2001 | Verschuur et al. | 235/462.25 |
| 6,215,508 B1 * | 4/2001 | Bryan et al. | 347/171 |
| 6,265,466 B1 | 7/2001 | Glatkowski et al. | |
| 6,329,813 B1 | 12/2001 | Andermo | |
| 6,372,293 B1 * | 4/2002 | Mathus et al. | 427/271 |
| 6,435,175 B1 | 8/2002 | Stenzler | |
| 6,475,192 B1 * | 11/2002 | Reilly et al. | 604/189 |
| 6,533,183 B2 * | 3/2003 | Aasmul et al. | 235/494 |
| 6,652,812 B1 | 11/2003 | Vartiainen et al. | |
| 6,669,090 B2 * | 12/2003 | Eilersen | 235/462.03 |
| 6,813,868 B2 * | 11/2004 | Baldwin et al. | 53/411 |
| 6,854,653 B2 * | 2/2005 | Eilersen | 235/462.03 |
| 6,957,522 B2 * | 10/2005 | Baldwin et al. | 53/411 |
| 6,976,349 B2 * | 12/2005 | Baldwin et al. | 53/468 |
| 6,994,261 B2 * | 2/2006 | Eilersen | 235/487 |
| 7,018,363 B2 * | 3/2006 | Cowan et al. | 604/181 |
| 7,041,941 B2 * | 5/2006 | Faries et al. | 219/413 |
| 7,061,831 B2 * | 6/2006 | De La Huerga | 368/10 |
| 7,077,332 B2 * | 7/2006 | Verschuur et al. | 235/492 |
| 7,108,184 B2 * | 9/2006 | Mase et al. | 235/462.01 |
| 2001/0001472 A1 * | 5/2001 | Sano et al. | 235/462.01 |
| 2001/0013544 A1 * | 8/2001 | Rathus et al. | 235/380 |
| 2001/0015202 A1 * | 8/2001 | Miller, Jr. | 128/204.21 |
| 2001/0034506 A1 | 10/2001 | Hirschman et al. | |
| 2002/0000471 A1 * | 1/2002 | Aasmul et al. | 235/462.45 |
| 2002/0012176 A1 | 1/2002 | Ning | |
| 2002/0020654 A1 * | 2/2002 | Eilersen | 206/570 |
| 2002/0022821 A1 * | 2/2002 | Eilersen | 604/404 |
| 2002/0063156 A1 * | 5/2002 | Marchand | 235/462.01 |
| 2002/0106309 A1 | 8/2002 | Mathus et al. | |
| 2002/0117549 A1 | 8/2002 | Lee | |
| 2002/0117579 A1 | 8/2002 | Kotoulas et al. | |
| 2002/0123078 A1 * | 9/2002 | Seul et al. | 435/7.2 |
| 2003/0015590 A1 * | 1/2003 | Chen | 235/494 |
| 2003/0039590 A1 | 2/2003 | Lodge | |
| 2003/0116630 A1 * | 6/2003 | Carey et al. | 235/462.09 |
| 2003/0143614 A1 * | 7/2003 | Drmanac | 435/6 |
| 2003/0205625 A1 * | 11/2003 | Eilersen | 235/494 |
| 2003/0233069 A1 | 12/2003 | Gillespie, Jr. et al. | |
| 2004/0008853 A1 | 1/2004 | Pelrine et al. | |
| 2004/0024368 A1 * | 2/2004 | Broselow | 604/207 |
| 2004/0046032 A1 * | 3/2004 | Urano et al. | 235/468 |
| 2004/0051368 A1 | 3/2004 | Caputo et al. | |
| 2004/0141426 A1 * | 7/2004 | Kawasaki et al. | 369/13.17 |
| 2004/0155113 A1 * | 8/2004 | Urano et al. | 235/491 |
| 2004/0200558 A1 * | 10/2004 | Stevens et al. | 156/64 |
| 2004/0207385 A1 | 10/2004 | Gafner et al. | |
| 2004/0210199 A1 * | 10/2004 | Atterbury et al. | 604/224 |
| 2005/0006472 A1 * | 1/2005 | Verschuur et al. | 235/451 |
| 2005/0035207 A1 * | 2/2005 | Philyaw et al. | 235/462.42 |
| 2005/0060059 A1 * | 3/2005 | Klein et al. | 700/213 |
| 2005/0116033 A1 * | 6/2005 | Moore | 235/385 |
| 2005/0156318 A1 * | 7/2005 | Douglas | 257/761 |
| 2005/0236603 A1 * | 10/2005 | Faris | 252/500 |
| 2005/0283116 A1 * | 12/2005 | Eakins et al. | 604/111 |
| 2006/0097877 A1 * | 5/2006 | Baba et al. | 340/572.4 |
| 2006/0118612 A1 * | 6/2006 | Christoffersen et al. | 235/375 |
| 2006/0125491 A1 * | 6/2006 | Grishin et al. | 324/663 |
| 2006/0129104 A1 * | 6/2006 | Cowan et al. | 604/181 |
| 2006/0138233 A1 * | 6/2006 | Kemppainen et al. | 235/451 |
| 2006/0164002 A1 * | 7/2006 | O'Brien et al. | 313/498 |
| 2006/0170981 A1 * | 8/2006 | Ricks et al. | 358/3.32 |
| 2006/0176267 A1 * | 8/2006 | Honeyman et al. | 345/107 |
| 2006/0226238 A1 * | 10/2006 | Salib et al. | 235/492 |
| 2006/0243804 A1 | 11/2006 | Christoffersen et al. | |
| 2007/0080234 A1 * | 4/2007 | Domoy | 235/494 |
| 2009/0088701 A1 * | 4/2009 | Larsen | 604/189 |

FOREIGN PATENT DOCUMENTS

| | | |
|---|---|---|
| DE | 19504111 | 8/1995 |
| EP | 0 235 691 A2 | 2/1987 |
| EP | 0235691 | 2/1987 |
| EP | 248165 | 12/1987 |
| EP | 0 364 010 B1 | 4/1993 |
| EP | 0364010 | 4/1993 |
| EP | 685810 | 12/1994 |
| EP | 0690457 | 5/1995 |
| EP | 0 336 778 B1 | 12/1995 |
| EP | 0336778 | 12/1995 |
| EP | 716290 | 6/1996 |
| EP | 0 492 954 B1 | 10/1996 |
| EP | 0492954 | 10/1996 |
| EP | 0 833 278 A2 | 4/1998 |
| EP | 0833278 | 4/1998 |

| | | |
|---|---|---|
| EP | 0 573 129 B1 | 8/1998 |
| EP | 0573129 | 8/1998 |
| EP | 0911859 | 10/1998 |
| EP | 0 588 427 B1 | 11/1998 |
| EP | 0588427 | 11/1998 |
| EP | 1 142 643 A3 | 10/2001 |
| EP | 1 143 643 A3 | 10/2001 |
| EP | 1142643 | 10/2001 |
| EP | 1143643 | 10/2001 |
| EP | 1246127 | 3/2002 |
| EP | 1 193 641 A3 | 4/2002 |
| EP | 1193641 | 4/2002 |
| GB | 2 088 163 A | 6/1982 |
| GB | 2088163 | 6/1982 |
| GB | 2 216 259 A | 10/1989 |
| GB | 2216259 | 10/1989 |
| GB | 2 287 551 A | 9/1995 |
| GB | 2287551 | 9/1995 |
| GB | 2 309 801 A | 8/1997 |
| GB | 2309801 | 8/1997 |
| GB | 2 341 965 A | 3/2000 |
| GB | 2341965 | 3/2000 |
| JP | 05-314296 | 11/1993 |
| JP | 9-91364 | 7/1995 |
| JP | 07-271890 | 10/1995 |
| JP | 09-034361 | 2/1997 |
| JP | 9-91364 | 4/1997 |
| JP | 09-223181 | 8/1997 |
| JP | 09-274637 | 10/1997 |
| JP | 11-316877 | 11/1999 |
| JP | 2000-272191 | 3/2000 |
| JP | 2001-043301 | 2/2001 |
| JP | 2001-075480 | 3/2001 |
| JP | 2002-082120 | 3/2002 |
| WO | WO 93/12828 | 7/1993 |
| WO | WO 94/08647 | 4/1994 |
| WO | WO 94/12235 | 6/1994 |
| WO | WO 95/28190 | 10/1995 |
| WO | 00/42678 | 1/2000 |
| WO | WO 00/42678 | 1/2000 |
| WO | WO 01/22348 | 3/2001 |
| WO | WO 01/54055 | 7/2001 |
| WO | WO 01/62322 | 8/2001 |
| WO | WO 02/13133 | 8/2001 |
| WO | WO 01/70304 | 9/2001 |
| WO | WO 01/84542 | 11/2001 |
| WO | 02/11792 | 2/2002 |
| WO | 02/13133 | 2/2002 |
| WO | WO 02/11792 | 2/2002 |
| WO | WO 02/095675 | 11/2002 |
| WO | WO 03/017915 | 3/2003 |
| WO | WO 03/020598 | 3/2003 |
| WO | WO 03-020598 | 3/2003 |
| WO | WO 03/038738 | 5/2003 |
| WO | WO 2004/084795 | 10/2004 |
| WO | WO 2004/097715 | 11/2004 |
| WO | WO 2005/089835 | 9/2005 |

OTHER PUBLICATIONS

Office Action dated Jan. 4, 2008 from U.S. Appl. No. 11/396,889, an application filed Apr. 3, 2006 by Christoffersen et al.
English language abstract of JP 2001-043301.
English language abstract of JP 2000-272191 (provided by EPO).
English Language Abstract of DE 3712089.
English Language Abstract of JP 2001-075480.
English Language Abstract of JP 2002-082120.
English Language Abstract of JP 05-314296.
English Language Abstract of JP07-271890.
English Language Abstract of JP 09-223181.
English Language Abstract of JP 09-274637.
English Language Abstract of JP 11-316877.
English Language Abstract of WO 0122348.
Office Action dated Jan. 4, 2008 from U.S. Appl. No. 11/396,889, an application filed Apr. 3, 2006 by Christoffersen et al.

* cited by examiner

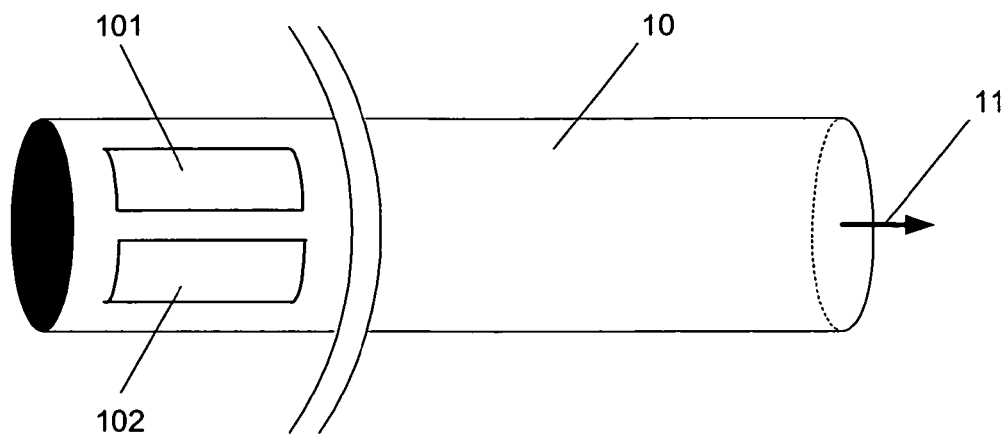
Fig. 1.a
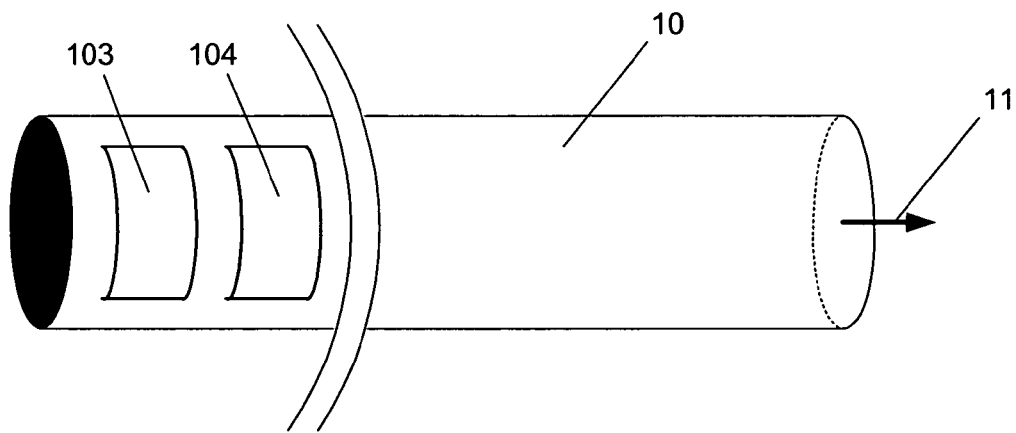
Fig. 1.b
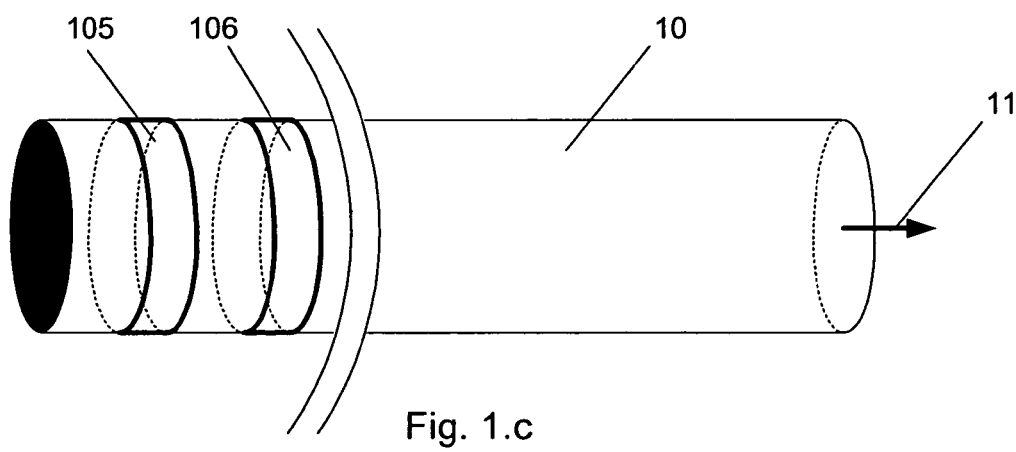
Fig. 1.c

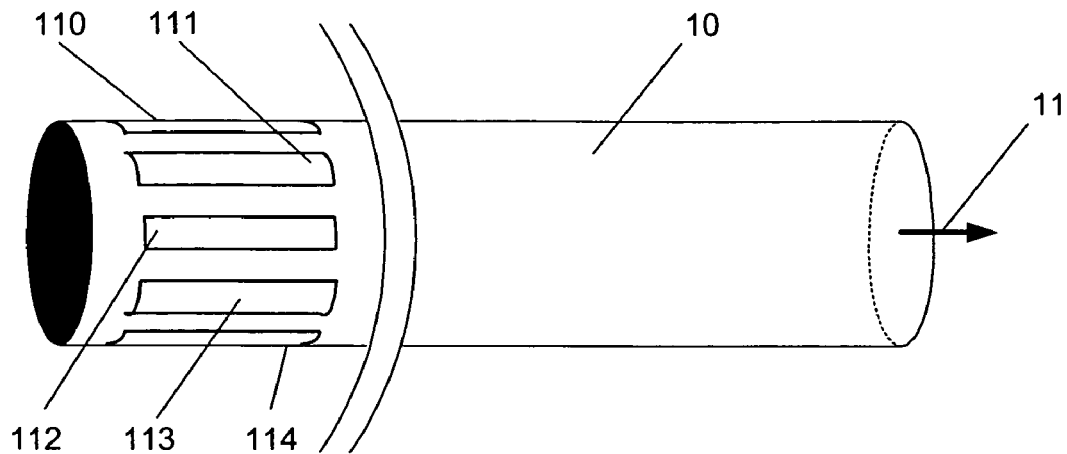
Fig. 1.d
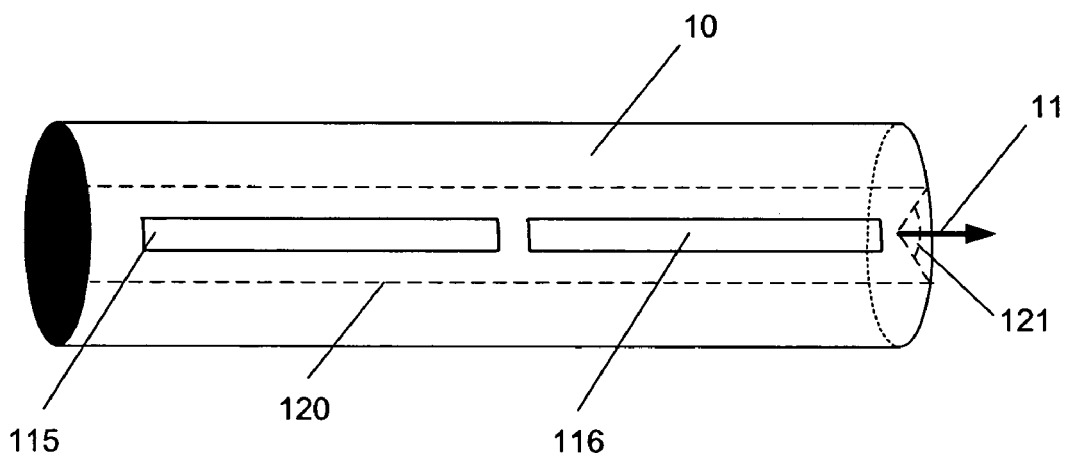
Fig. 1.e
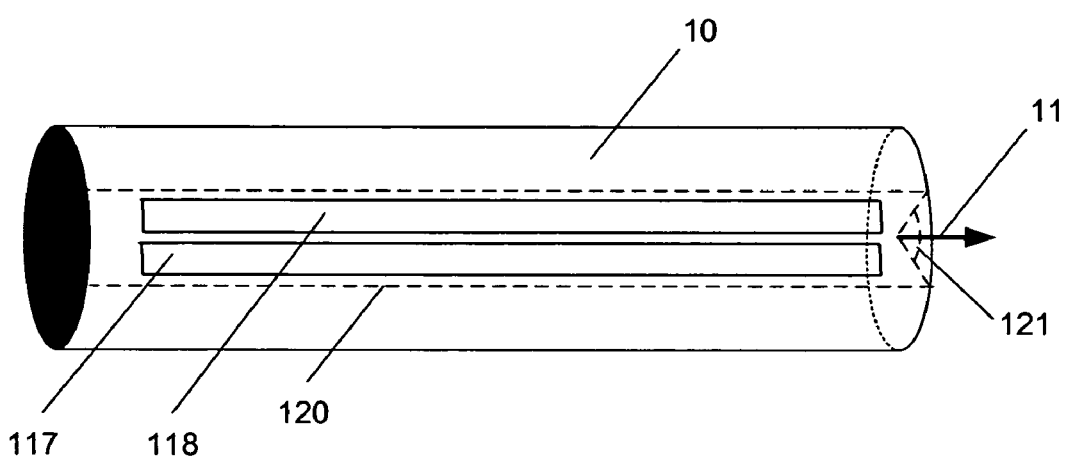
Fig. 1.f

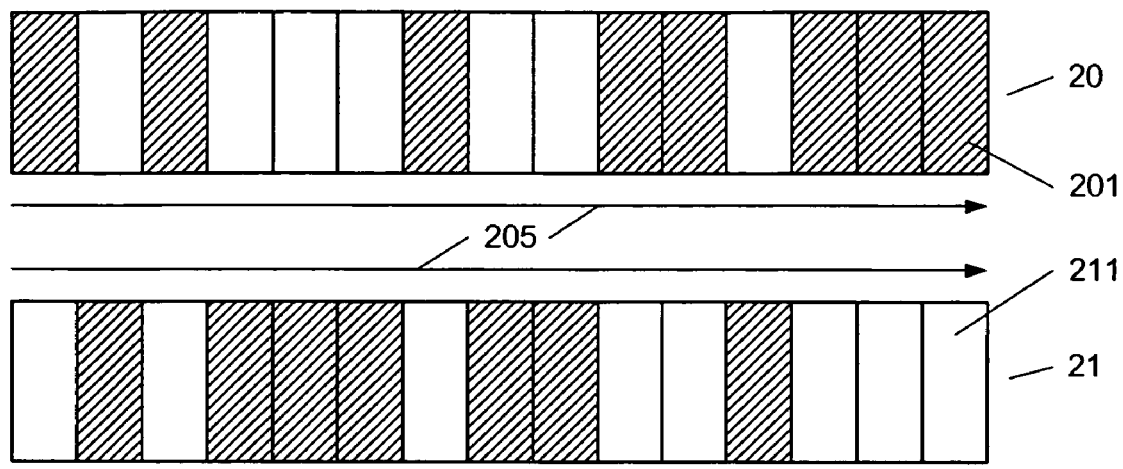
Fig. 2.a
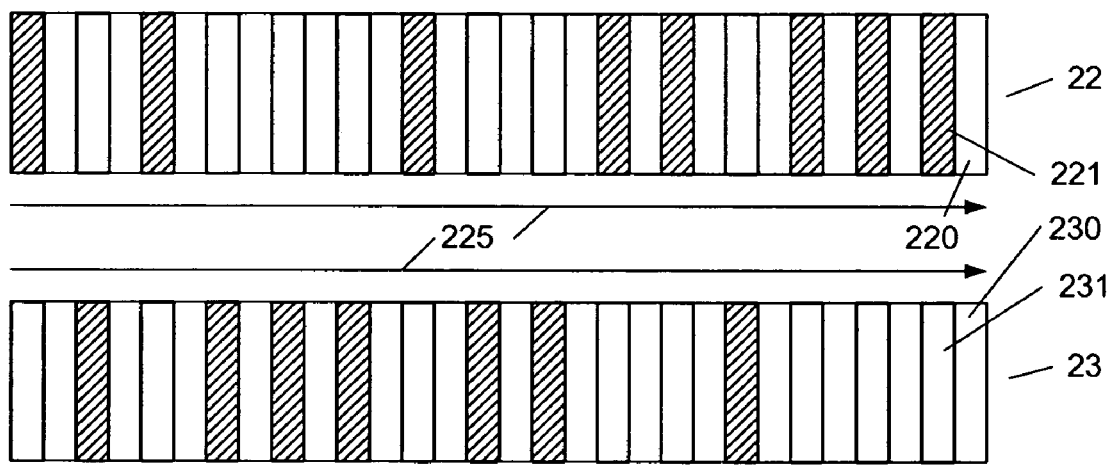
Fig. 2.b

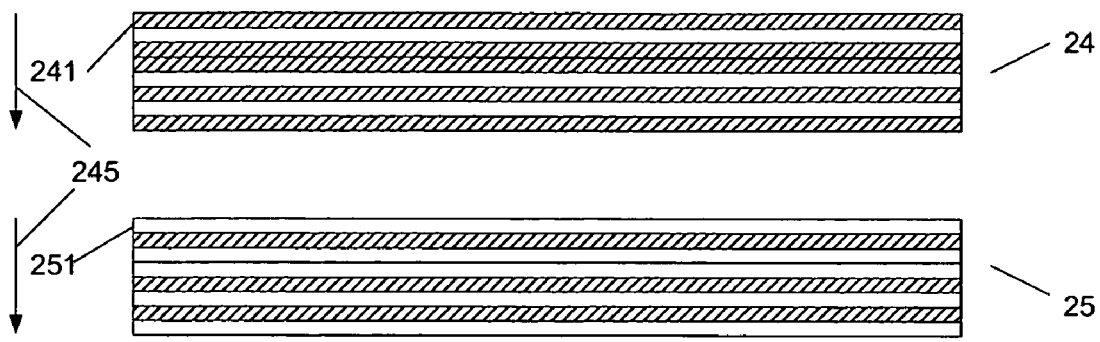
Fig. 2.c
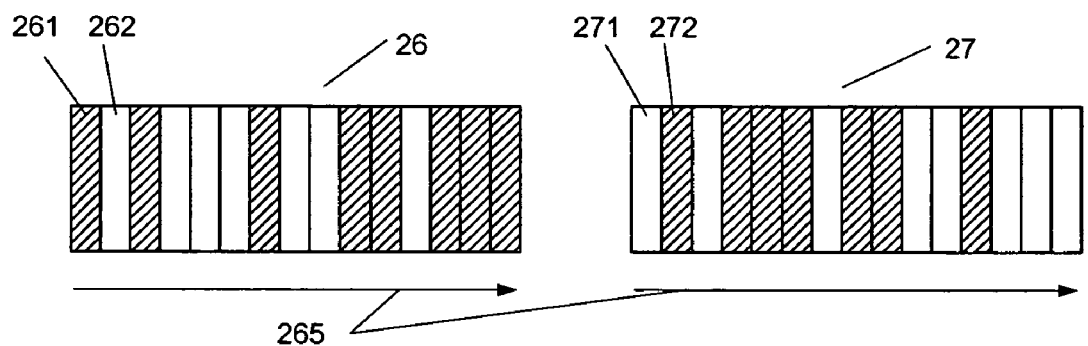
Fig. 2.d
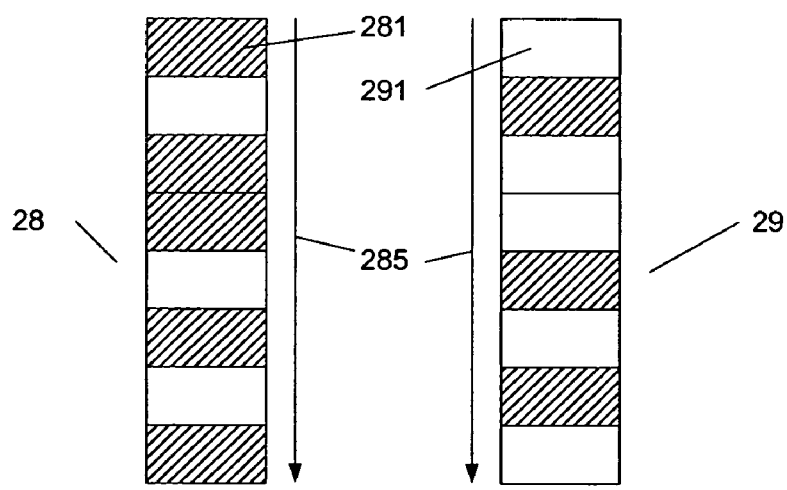
Fig. 2.e

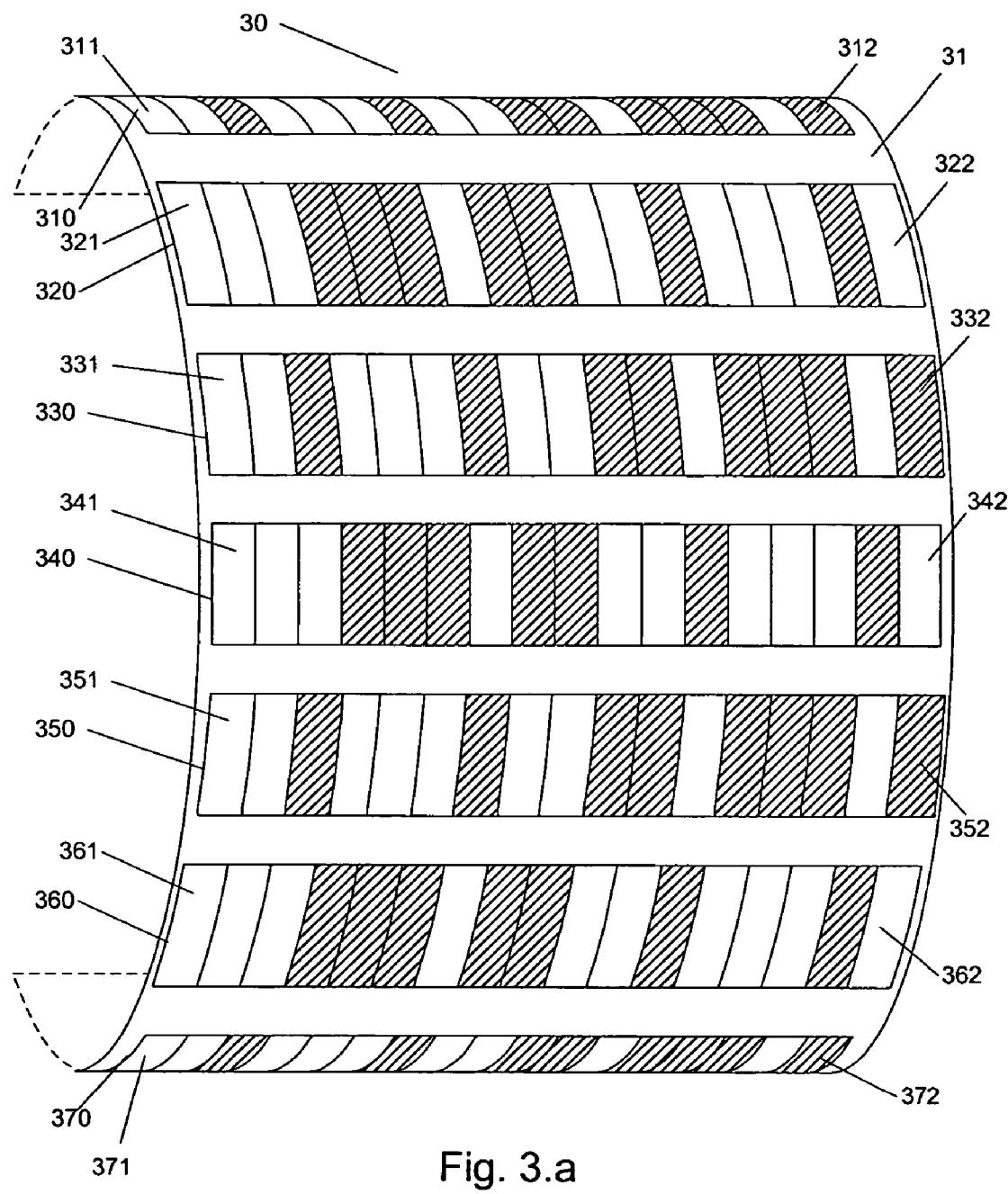
Fig. 3.a

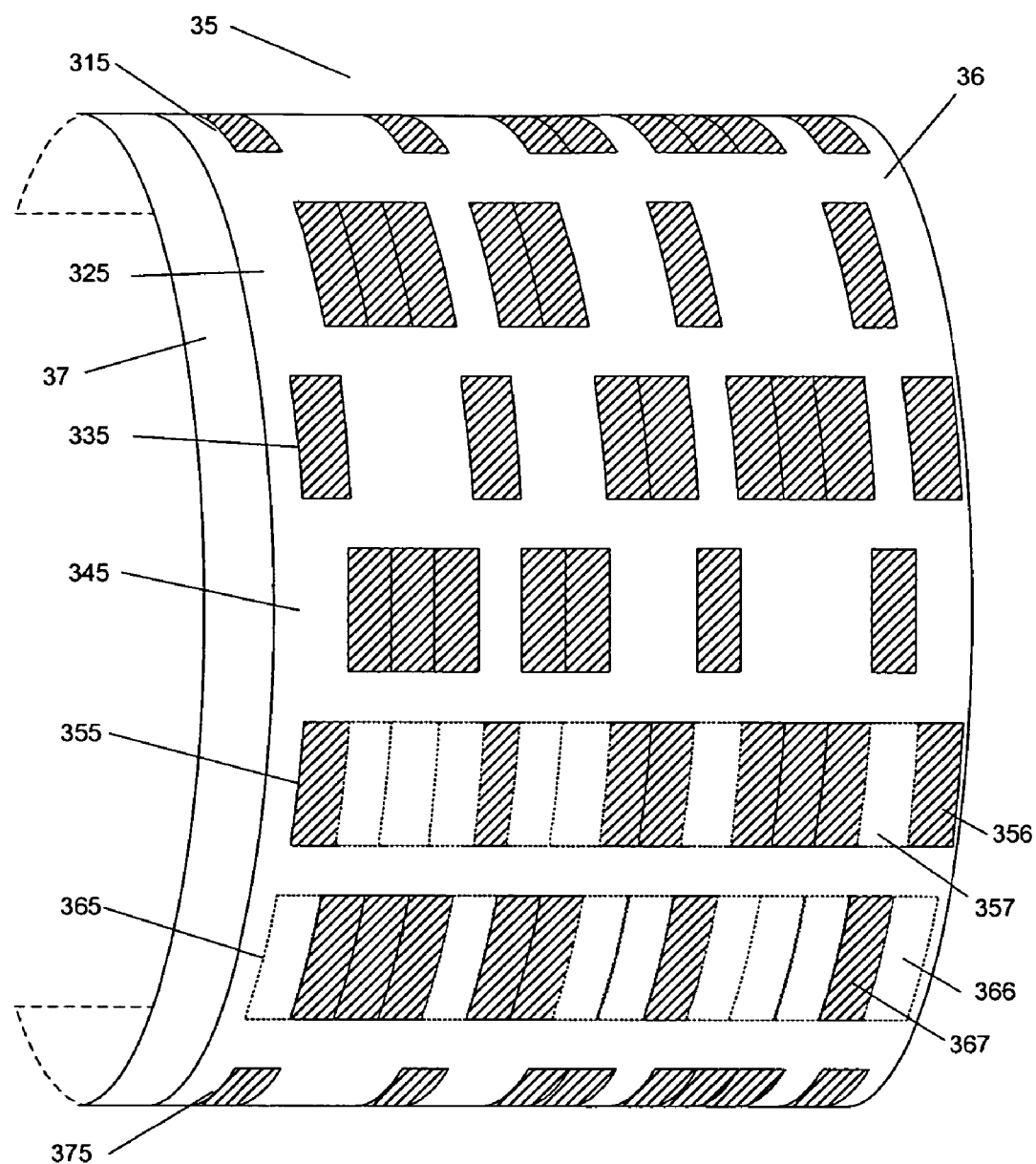
Fig. 3.b

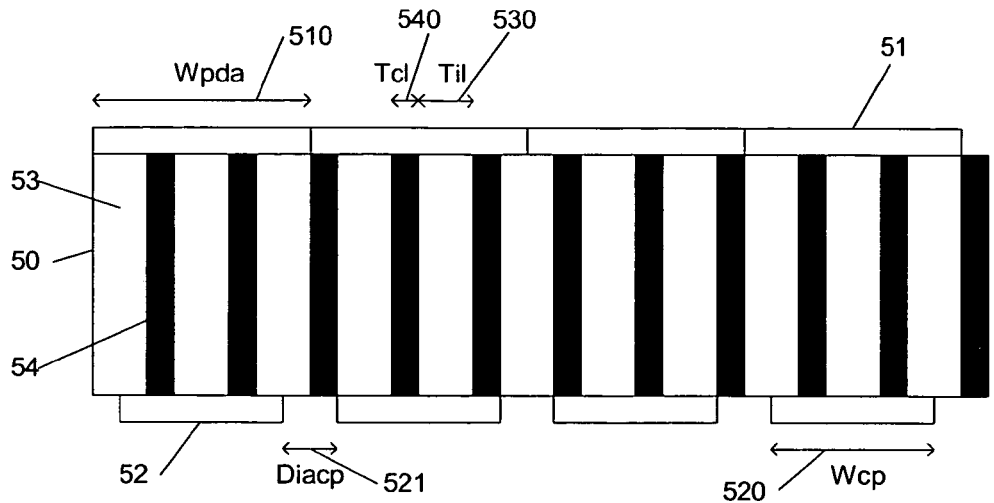
Fig. 5.a
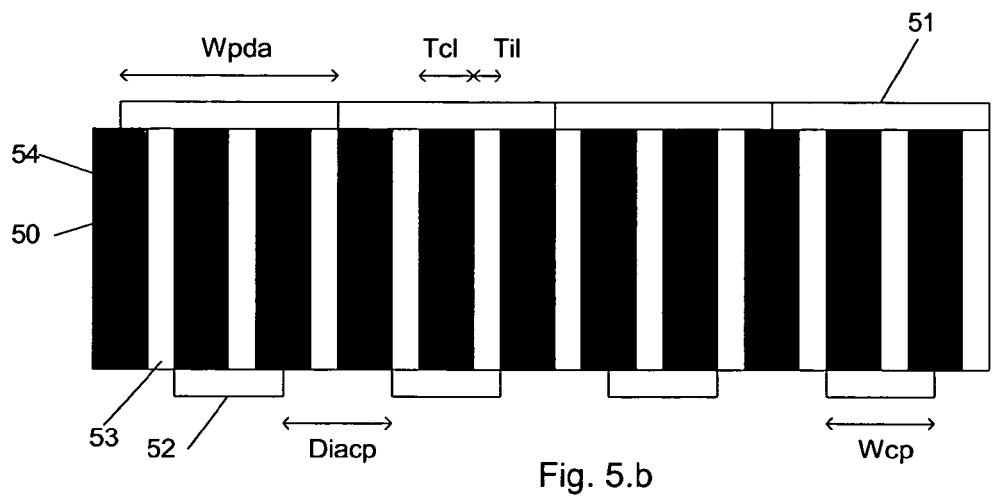
Fig. 5.b
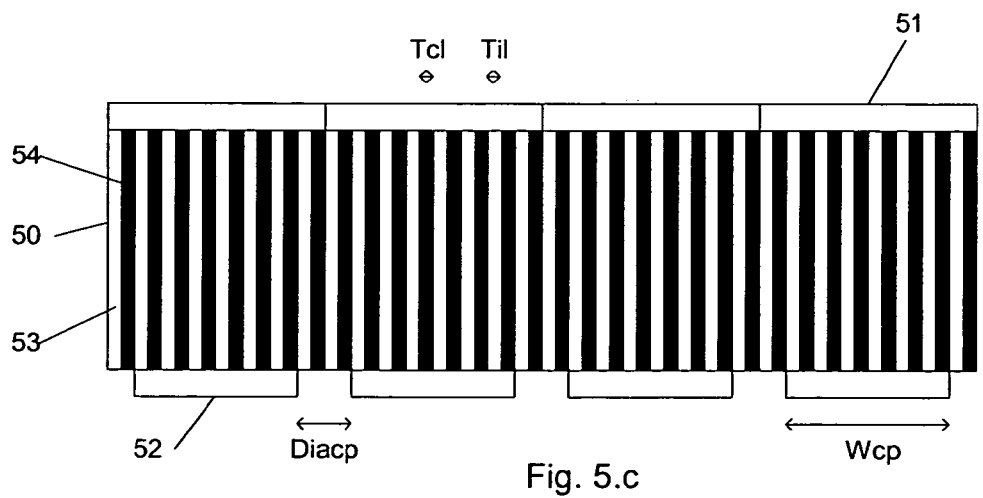
Fig. 5.c

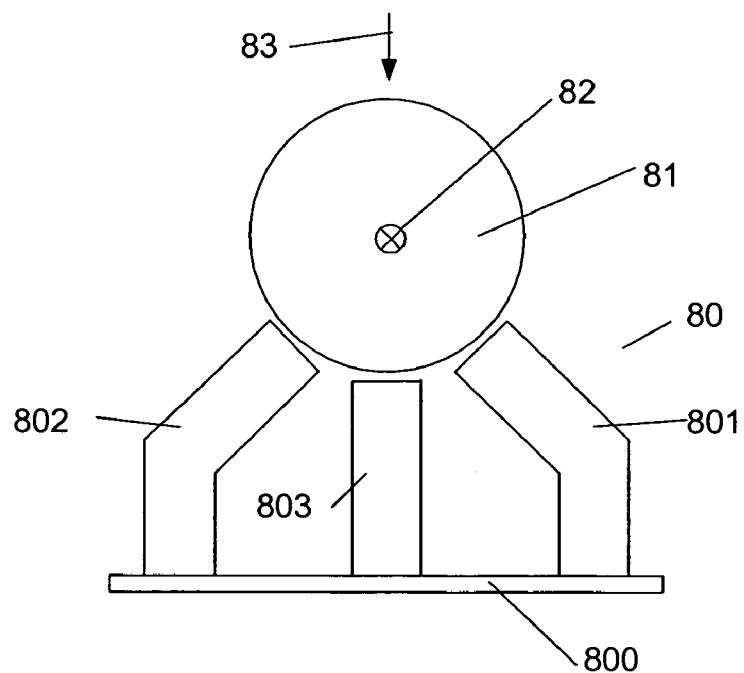
Fig. 8.a
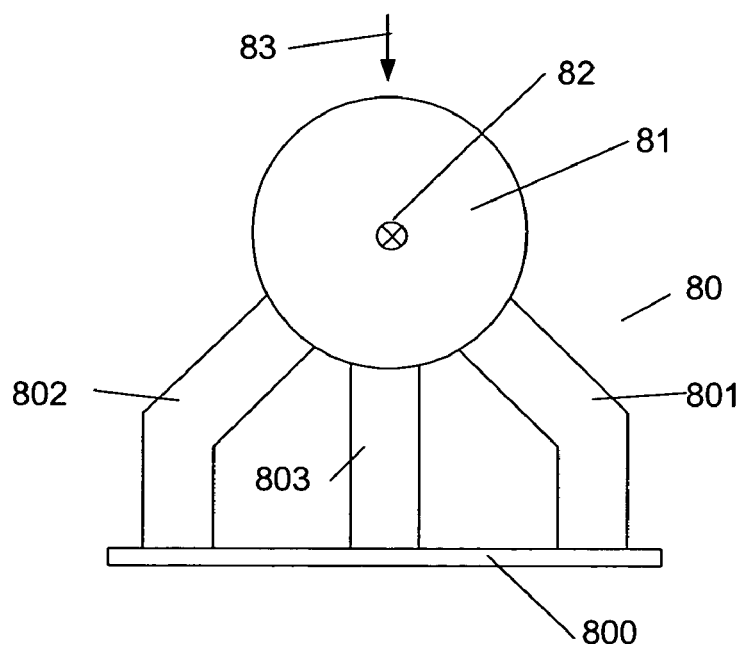
Fig. 8.b

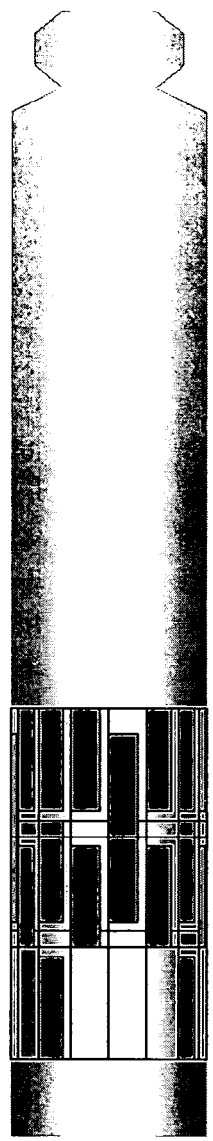
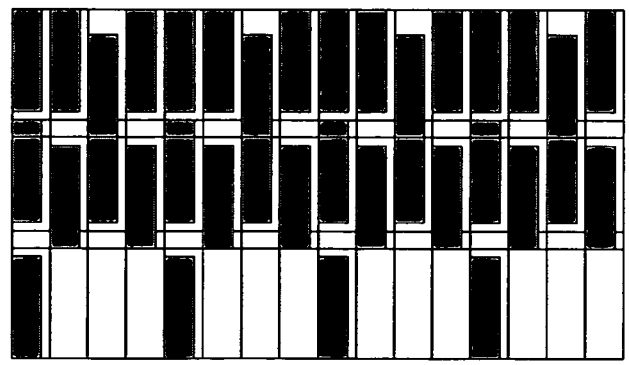
Figure 11.

ELECTRONIC MARKING OF A MEDICATION CARTRIDGE

CROSS-REFERENCE TO RELATED APPLICATIONS

This application is a continuation of International Patent Application PCT/DK2004/000199 (published as WO 2004/084795), filed Mar. 23, 2004, which claimed priority of Danish Patent Application PA 2003 00448 filed, Mar. 24, 2003; this application further claims priority under 35 U.S.C. § 119 of U.S. Provisional Application No. 60/457,180 filed Mar. 25, 2003.

THE TECHNICAL FIELD OF THE INVENTION

The invention relates to the electronic marking of medication cartridges or the like.

The invention relates specifically to: A medium such as a cartridge, a carpule, a label or a package provided with one or more electronically readable information carrying areas.

The invention also relates to: A method of providing an electronically readable item of information on a medication cartridge.

The invention furthermore relates to: A medication cartridge with an information-providing source containing an electronically readable item of information.

DESCRIPTION OF RELATED ART

The following account of the prior art relates to one of the areas of application of the present invention, the electronic marking of medication cartridges, carpules or packages.

In applications of medication delivery devices for self-treatment of a disease, e.g. diabetes, cartridges containing medication for a certain number of doses are mounted in the delivery device and exchanged with a new one when empty or when another medication is to be used according to the particular situation. It is of paramount importance that the medication used is the intended one, that it is not too old, that it has the correct concentration etc. Therefore the marking of the cartridge containing the medication has to be given special attention. To aid the user in achieving a satisfactory level of security in the use of a medication delivery device, a marking of the cartridge in addition to a traditional alphanumeric inscription has been introduced. Apart from information on the contents of the cartridge, the item of information may hold technical data on the type of cartridge, outlet dimension or other information of relevance to the medication delivery process.

U.S. Pat. No. 5,954,700 discloses a cartridge for containing a fluid and for use with an electronic delivery device which includes a cartridge housing for holding the fluid, and an information providing source. The information-providing source may be a set of wires and contacts, or contact bands that provide the predetermined information to an electronic delivery device by producing a binary code.

EP 0 911 859 A1, EP 0 690 457 A2 and U.S. Pat. No. 6,265,466 B1 disclosed different kinds of transparent conductors.

WO 00/42678 discloses the use of transparent electrostatic electrodes and transparent conductive material in combination with radio frequency identification. These electrodes are used in electronic surveillance systems, where it is possible to identify whether a marked object is passing a fixed location or not. These kinds of marking can be used for medical containers, where they are a part of an automatic process. This method has the setback that either a relatively expensive chip is needed in the marked object or otherwise it does not provide any information on the content, the expiry date etc, of the container, it only tells whether the object is passing a certain location or not.

The possible spill of drops of the medication from the medication cartridge may typically deteriorate the readability of the optically readable or electronically readable coded information on the cartridge due to chemical reactions. This calls for a method of marking which is robust and does not allow the introduction of errors in the interpretation of the coded information in case of minor deteriorations of the code in question.

WO 02/13133 discloses a method of providing an electronically readable item of information on a cartridge and how to transfer this information to an electronic circuit. The marking of the cartridge is in form of conductive structures/patterns on the surface. The pattern is divided into areas, encoding elements, each containing a piece of information. The marking can be detected by a sensor/contact array placed inside a drug delivery device such as an insulin pen injector or an insulin pump.

In one preferred embodiment the marking is placed at the cartridge label. Such a label is found on cartridges for durable delivery systems devices, where the used and emptied cartridges are continuously replaced with new cartridges. The label is the outermost surface of the cartridge and is therefore suitable for coupling with an array of sensing contact electrodes. The label contains printed text with information to the patient and health care personnel, for example drug type and concentration, as well as manufacturing and expiry date. In many cases most of the label area is covered by text due to regulatory demands on the required information.

If the conductive structures are placed on the label on top of the text, the reading of the printed text is likely to be disturbed. For reasons which are described below it is not possible to increase the size of the label. Therefore the marking must be confined to a small area on the cartridge surface, and preferably around the piston position of a full cartridge. In other words a certain area of the medication cartridge must be reserved to hosting an increasing amount of information.

Another remedy for avoiding errors and for making the user feel comfortable with the handling is that the drug contained in the medication cartridge is visible from outside, so that the user is able to check the color, the uniformity, whether impurities are present, etc. For this reason, as large a part of the surface of the medication cartridge as possible should be free of opaque items such as metallic conductors, which limit a user's view of the contents.

Further, there is a general trend to miniaturization of electronic devices including medication delivery devices, so that they are easy to carry and discreet in use.

It is important that the drug delivery device is able to read the information carrying areas without errors. A restricted information carrying area increases the information density of the marking and therefore increases the demand for the mechanical precision of the coupling between the marking and the contact array. These demands can be difficult to meet on mass produced cartridges, carpules or packages.

Therefore there is a need for an electronically readable marking which allows visual inspection of a cartridge, a carpule or a package, allows reading of a mandatory text and where the marking area is sufficiently large to overcome both problems with orientation of the container and sensibility of the sensor.

DISCLOSURE OF THE INVENTION

Thus, the object of the present invention is to provide an improved method of marking a medium.

The present invention is a new way of marking a medium such as cartridges, carpules, labels or any kind of package allowing both visual inspection of the content of the item and automatic identification of the content. In this invention transparent conductive material is used to form a pattern which is composed of smaller areas of conducting and/or non-conducting areas, and the patterns contain any desirable information e.g. the drug type, the concentration, the expiry date and etc.

The term transparent means that in a region of the light spectrum it is possible to see through the marking. The area of light, where the marking is transparent, is preferably the visible area of light. Alternatively the marking can additionally be transparent or non-transparent in the UV and/or IR area.

Hereby it is possible to have a label which can be put on any package, with the mandatory text, the area for visual inspection of the content of the item and still have a large area for the sensing contact electrodes.

With this new possibility of increasing the area of the electronically readable area, without limiting visual inspection of the content or having any impact on the reading of the text, the reading equipment does not need the same sensitivity and precision. Therefore cheaper sensing equipment can be used and the same degree of security is maintained.

Furthermore the orientation of the cartridge is no longer confined to have the previously small information area pointing towards the sensor arrays. Now it is possible if desired to print the information all over the cartridge, the carpule or the package and therefore there is no limitation to the orientation of the container.

This is achieved according to the invention in that said item of information is redundantly provided. In this way, a very simple method is provided that may be implemented in a multitude of ways, customized to each specific application.

In the present context, the term 'cartridge' is taken to mean a container for holding a liquid or powder or other matter of a size and weight that can be handled by hand. The cartridge may e.g. be a cartridge containing medication for use with a medication delivery system for self-treatment of a disease. The medication in the cartridge may e.g. be insulin for use with a pen-type injection system for treating diabetes.

The term 'carpule' is a special form of cartridges used for medical products.

In a preferred embodiment said item of information is provided at least once in a binary true and inverted form.

In the present context, the term 'redundantly provided in a binary true and inverted form' is taken to mean that the information is provided in a way that may be directly translated to a binary representation (e.g. 100110) and that the same item of information is provided in its true (e.g. 100110) and inverted (011001) form, yielding a redundancy that may be used to check the validity of the electronically read code. I.e. if e.g. one or more of the ('should be') inverted bits equals the corresponding bits of the true representation, an error is present. This check gives a higher degree of safety in interpreting the item of information in question which e.g. is important when the container is used for medication in connection with a person's self-treatment of a disease.

Apart from the above mentioned redundancy, each item of information (in its binary true or inverted forms) may be subject to standard error detecting measures, such as reserved bits for a parity check, a CRC (Cyclic Redundancy Check) or the like, and/or error correcting measures.

When said item of information is provided in any one of its binary forms by forming electrically insulating and electrically conducting areas corresponding to the relevant state of each bit of information in predefined positions on the surface of the cartridge, it is ensured that a very simple, flexible and inexpensive method is provided.

When said medication cartridge has an axis of rotational symmetry, it is ensured that a reading procedure that is independent of the rotational orientation of the cartridge is possible. This makes the positioning procedure of the cartridge in the medication delivery device convenient for the user in that he or she does not have to think about its correct orientation in the circumferential direction, defined as a circumference on the surface of the cartridge in a direction perpendicular to the axis of symmetry (also termed the 'radial direction' in the following).

When said electrically insulating or electrically conducting areas fully or partially circumfere said axis of symmetry, thus defining two or more information carrying areas, each containing said item of information in its binary true or inverted form, on said cartridge, it is ensured that the reading of the information may be made independent of the radial orientation of the cartridge.

When said electrically insulating or electrically conducting areas are positioned in one or more longitudinal areas stretching in the direction of said axis of symmetry, each longitudinal area covering only a fraction of the circumference of said cartridge, thus defining two or more information carrying areas, each containing said item of information in its binary true or inverted form, on said cartridge, it is ensured that information carrying areas may be evenly distributed in the radial direction of the cartridge, and thereby making the reading of the information independent or nearly independent of the radial orientation of the cartridge.

When said item of information is provided in any one of its binary forms by applying electrically insulating areas to predefined positions on an electrically conducting foil, said foil being positioned on said cartridge, it is ensured that a very simple and convenient method of adding an electronically readable item of information to a cartridge is provided, which method is well suited for mass production.

When said item of information is read by applying a voltage to said electrically conducting foil, said voltage corresponding to the supply voltage of one of the logic levels of a digital processing circuit, and by connecting each predefined position on the foil electrically with inputs to a digital processing circuit, it is ensured that a very simple and inexpensive method is provided that may take a variety of forms, customized to each specific application. It further has the advantage that no additional components or extra, customized wiring on the cartridge is necessary in order to define and electronically read a specific item of information.

When said inputs to the digital processing circuit are provided with pull-up or pull-down circuitry according to which of the supply voltages of the logic levels of said digital processing circuit is applied to said electrically conducting foil, it is ensured that a simple and easily producible scheme is provided.

When said inputs to the digital processing circuit may be selectably provided with either pull-up or pull-down circuitry according to which of the supply voltages of the logic levels of said digital processing circuit is correspondingly selectably applied to said electrically conducting foil, said selection being controlled by said digital processing unit, it is ensured that the probability of falsely reading the item of information in question is reduced.

When the redundant information from two or more information carrying areas on the cartridge is transferred to a contact area that is connected to a processing circuit by supporting means for the cartridge, the supporting means being at least partially constituted by two or more electrically connecting supports, each comprising a number of closely spaced mutually electrically insulated conductors embedded in an electrically insulating material that stretches from one of the supporting surfaces of the cartridge to a contact area for receiving and transferring the information to said processing circuit, when said cartridge is positioned in said support, it is ensured that a flexible method of simultaneously supporting the cartridge and transferring the information from the cartridge to a contact area for further processing is introduced.

When each of said two or more electrically connecting supports is constituted by alternating layers of electrically conducting material of maximum thickness $T_{cl}$ and electrically insulating material of maximum thickness $T_{il}$, respectively, it is ensured that a method well suited for transferring a high information density is disclosed. By controlling the dimensions of the layer thicknesses and the corresponding geometries of the contact area and the information carrying areas, the information density may be controlled, i.e. by shrinking the layer thicknesses, the information density may be increased. By using the transparent conductors, where a large coding area is possible, the thickness can be significantly larger than with the traditional conductors. The support is therefore cheaper to produce or alternatively a greater accuracy in the detection can be achieved.

When said alternating layers are made of elastic materials, it may be ensured that the electrically connecting supports conform to the shape of the cartridge when the cartridge is positioned in the support with a certain minimum pressure. I.e. it makes the support even more flexible and relaxes the tolerances to its conformity with the cartridge and with the contact area (e.g. pads on a printed circuit board (PCB) for connecting to a processing circuit on the PCB).

A medication cartridge with an information-providing source containing an electronically readable item of information is moreover provided by the present invention. When said item of information is redundantly provided at least once by applying electrically insulating and electrically conducting areas corresponding to the relevant state of each bit of information in predefined positions on the surface of the cartridge, it is ensured that a cartridge containing an electronically readable item of information implemented in a simple way is provided, which cartridge is well suited for being part of a system that requires a high safety in information transfer, such as e.g. a medication delivery system for self-treatment of a disease.

When said item of information is formed on a self-adhesive carrier positioned on the surface of the cartridge, it is ensured that a simple and convenient means for providing an item of information to a cartridge is provided.

In a preferred embodiment said cartridge has an axis of rotational symmetry.

In a preferred embodiment information carrying areas containing said item of information in its true and inverted forms, respectively, are positioned side by side in the direction of said axis of symmetry of said cartridge.

In a preferred embodiment information carrying areas containing said item of information in its true and inverted forms, respectively, are positioned side by side in the direction of a circumference of said axis of symmetry of said cartridge.

In a preferred embodiment information carrying areas are in form or larger and smaller areas. A combination of areas e.g. two small areas followed by a large (see FIG. 9) then code for e.g. concentration. The possible combinations of areas and information is almost unlimited and therefore a suitable way of coding.

When information carrying areas containing said item of information in its true and inverted forms, respectively, appear alternating a multitude of times in a direction of a circumference of said axis of symmetry of said cartridge, it is ensured that the same item of information is provided redundantly and repeatedly, which potentially facilitates the reading process. Furthermore, when a rotational symmetry is introduced, a reading procedure that is independent of the rotational orientation of the cartridge is possible.

When said item of information is provided in any of its binary forms by applying electrically insulating areas in predefined positions on the surface of an electrically conducting foil positioned on said cartridge in such a way that an electrically insulating area is applied at those predefined positions representing one predefined binary state, and an electrically conductive area is provided at those predefined positions representing the complementary binary state, it is ensured that a simple, flexible and economic configuration for electrically transferring an item of information from a cartridge to a processing means is provided.

When said item of electronically readable information is provided on the cartridge in an optically readable form, it is ensured that the item of information included on the cartridge for being electronically read may be read also directly by a user and/or by an optical scanner. Optionally the marking can be done with a material which is transparent in the area of visible light and gives a response in the UV or IR area of light. Hereby a transparent marking which is optically readable is obtained.

A support for a medication cartridge provided with an electronically readable item of information is furthermore provided. When said item of information being redundantly provided at least once by forming at least two information carrying areas containing electrically insulating and electrically conducting areas corresponding to the relevant state of each bit of information in predefined positions on the surface of said cartridge, and said support for the cartridge is at least partially constituted by two or more electrically connecting supports, each comprising a number of closely spaced mutually electrically insulated conductors embedded in an electrically insulating material that stretches from one of the supporting surfaces of the cartridge to a contact area for receiving and transferring the information to a processing circuit, when said cartridge is positioned in said support, it is ensured that the item of information on the cartridge may be transferred to an electronic circuit via an 'adapter' that may be adjusted to the particular embodiment of the cartridge and the physical device which it is part of.

When each of said two or more electrically connecting supports is constituted by alternating layers of electrically conducting material of maximum thickness $T_{cl}$ and electrically insulating material of maximum thickness $T_{il}$, respectively, it is ensured that a simple and flexible solution is provided. By controlling the thicknesses of the two layer types, the maximum density of information may be controlled.

When said cartridge has an axis of rotational symmetry, and said contact area consists of groups of identical and regularly spaced electrically conducting pads of width Wcp in the direction of adjacent pads, adjacent pads being separated by an electrically insulating area of width Diacp, and the following relations between said distances are fulfilled:

Diacp>2*$T_{cl}$, and

Wcp>$T_{il}$+$T_{cl}$, it is ensured that the electrical states of adjacent (possibly abutted) predefined positions are not transferred to the same pad (Diacp>2*$T_{cl}$), and that at least one conducting layer contacts any given pad (Wcp>$T_{il}$+$T_{cl}$).

When said cartridge has an axis of rotational symmetry, and said cartridge is provided with a multitude of rectangular, essentially parallel, identically sized information carrying areas of height Hica in the direction of a circumference of said axis of symmetry, said information carrying areas being spaced with equal mutual distance Dica along the periphery of the cartridge in the direction of a circumference of said axis of symmetry, and said supporting means comprise two rectangular, essentially parallel, identical electrically connecting supports of height Hctm in the direction perpendicular to the axis of symmetry of the cartridge, separated by an electrically insulating volume of width Dctm between the two electrically connecting supports, and the following relations between said distances are fulfilled:

Hica<Dctm<2*Hica+Dica, and

Hctm<Dica<2*Hctm+Dctm, it is ensured that the cartridge cannot be positioned in such a way that a given information carrying area has contact to two electrically connecting supports at the same time (Hica<Dctm). It is further ensured that the cartridge cannot be positioned in such a way that a given electrically connecting support has contact to two information carrying areas at the same time (Hctm<Dica). It is further ensured that the cartridge cannot be positioned in such a way that the electrically connecting supports fall entirely between two information carrying areas, in which case they would not have contact to any of the information carrying areas of the cartridge (Dica<2*Hctm+Dctm). It is further ensured that the cartridge cannot be positioned in such a way that two adjacent information carrying areas fall entirely between the electrically connecting supports, in which case the latter might not have contact to any of the information carrying areas of the cartridge (Dctm<2*Hica+Dica).

When said information carrying areas of height Hica each consists of electrically conducting and electrically insulating rectangular patches provided at said predefined positions on said cartridge according to a binary representation of said item of information, said patches having a width Wpda abut each other, and the sum of the maximum thicknesses $T_{cl}$ and $T_{il}$ of said alternating layers of electrically conducting and electrically insulating materials, respectively, constituting said electrically connecting supports, is less than the width Wpda of said patches, thus fulfilling the following relation between said distances:

Wpda>$T_{il}$+$T_{cl}$, it is ensured that each patch has contact to at least one of the conducting layers of an electrically connecting support when the cartridge is properly placed in the support.

BRIEF DESCRIPTION OF THE DRAWINGS

The invention will be explained more fully below in connection with a preferred embodiment and with reference to the drawings in which:

FIGS. 1.a-1.f show various ways of placing information carrying areas for holding electronically readable information on a cartridge, FIGS. 2.a-2.e show various ways of laying out the electrically conducting and electrically insulating areas in predefined positions within an information carrying area, implementing a binary representation of an item of information in its true and inverted form, FIGS. 3.a-3.b show labels according to the invention with a multitude of information carrying areas containing electrically conducting and electrically insulating areas in predefined positions, FIG. 11 shows a 4 times a 4 times 3 coding matrix applied to a cylindrical cartridge.

The figures are schematic and simplified for clarity, and they just show details, which are essential to the understanding of the invention, while other details are left out. In general, the reference numerals of a given drawing start with the number of that drawing, i.e. in FIG. 1, reference numerals typically have a 1 as the most significant digit (e.g. 1, 11, 102). This means on the other hand that functionally identical features occurring in different drawings have different reference numerals.

DETAILED DESCRIPTION OF EMBODIMENTS

Figure 4:
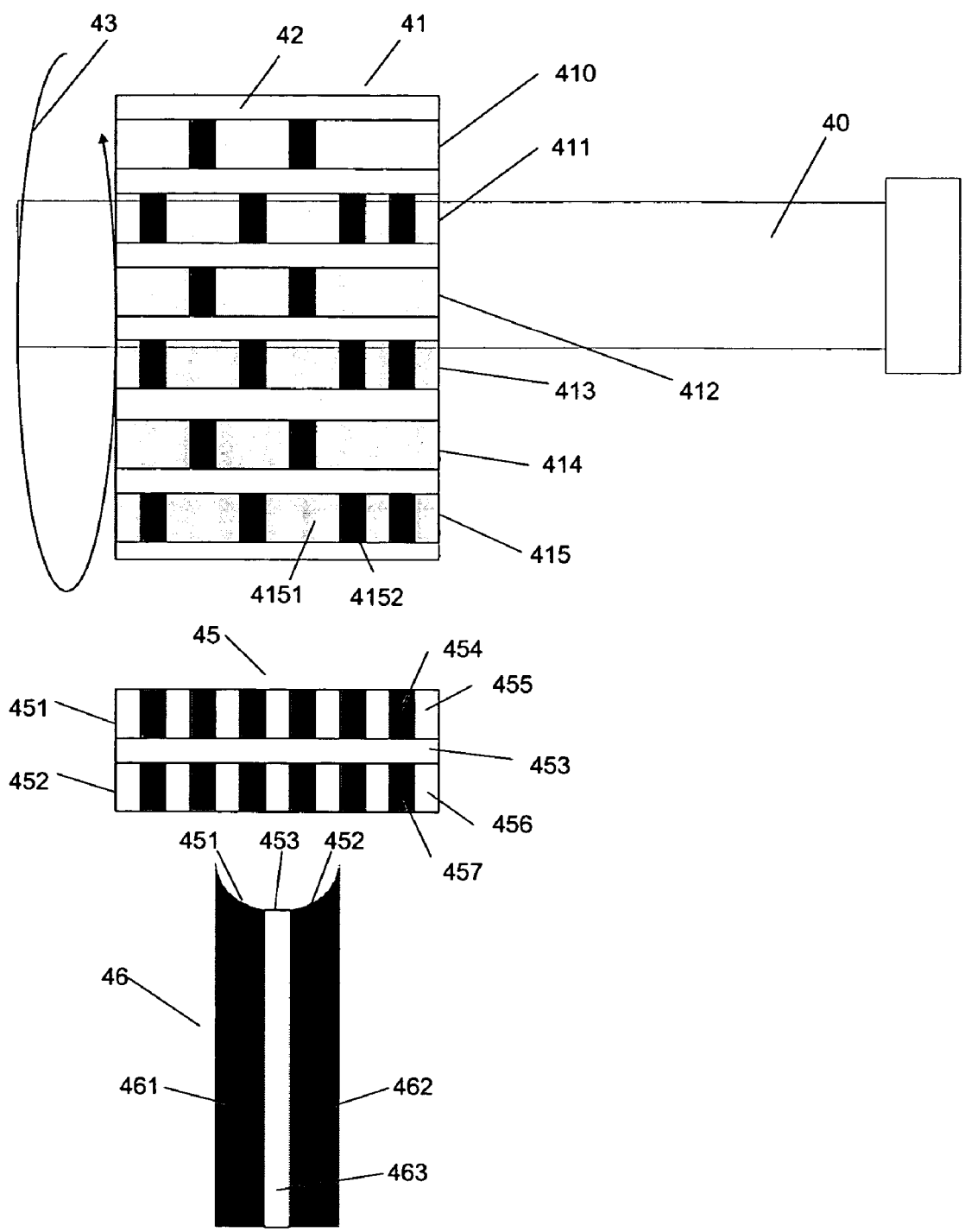
FIG. 4 shows a cartridge with a label containing an electronically readable information and a support for supporting the cartridge and for transferring the information from the cartridge to an electronic circuit, FIGS. 5.a-5.c show various geometries of an electrically connecting support according to the invention.

The present invention concerns the marking of a medium such as cartridges, carpules, labels or packages with a transparent conducting pattern e.g. in form of a matrix. The pattern has subunits which contain any kind of information and can be read by a sensor array e.g. in form of a contact electrode/contact electrodes. The measure can be done by, but are not limited to, a galvanic method.

A galvanic method has the advantage that it is easy, the sensing equipment is cheap, and there is a reduced risk of reading errors.

The item can be marked with the pattern in a number of ways. One way is to print the conductive pattern directly on the container as the outermost layer.

Another possibility is to print the transparent conductive pattern on a label, where said label can be either transparent or non-transparent. In case of being non-transparent, the label could first be, but is not limited to, printed with the mandatory text and then afterwards marked with the transparent pattern. In case of a transparent label, the label could be, but is not limited to, used as the outermost label optionally covering another label which has the mandatory text written on it. Since the conductor is transparent it is possible to read any text though the marking, just as it is possible to perform the visual inspection of the item.

Optionally the transparent conductive pattern is designed with an increased resistance to the rubbing and the general touching made both by man and equipment during use.

According to the invention there is provided a cartridges, a carpule or a package marked with a transparent conductor forming a pattern of elements suitable for encoding for the content of the item.

Furthermore, the invention provides a cartridge, a carpule or a package comprising a label marked with a transparent conductor forming a pattern of elements suitable for encoding for the content of the item.

The transparent conductive pattern can comprise transparent conductive polymers; e.g. Poly(3,4-ethylenedioxythiophene)-polystyrendesulphonate (PEDOT-PSS), polymers with networks of bis(ethylenedioxy) tetrathiafulvelene (BEDO-TFF)—iodine or bromine salt such as α-BEDO-TFF$_2$I$_3$, β-BEDO-TFF$_2$I$_3$, BEDO-TFF$_{2.4}$I$_3$ etc.; thin layers of Indium Tin Oxide (ITO) optionally mixed with one or more thin layer of silver. Furthermore, the transparent conductive pattern can contain conductive nanotubes dispersed in a polymer binder, noble metal particles with a size in the range 1-100 nm disposed in a polymeric binder as well as proton-doped polyanilin.

In another embodiment the pattern is provided by creating a transparent conductive film/coating, and then etching regions of the film/coating with an agent capable of destroying the conductive layer. The etching agent can be, but is not limited to, a combination of acid and an oxidizing agent, e.g. hydrochloric acid and CuCl$_2$.

The invention therefore also provides a process for producing a transparent conductor with elements suitable for storing information comprising the steps:

Coating at least a part of a surface with a transparent conductor patterning with etching.

Optionally the transparent conductor is printed upon with resist before the etching, and the resist is removed afterwards by a cleaner, e.g. alkaline solutions, preferably a strong alkali solution.

Preferably the patterning results in the surface being divided into conducting areas and non-conducting areas.

Optionally the etching agent can be a laser which removes the predetermined areas of the transparent conductor.

This invention is especially useful for marking medical containers such as cartridges, carpules and the like. The present invention makes it possible to have automatic checking of the content of the item, with a much cheaper and less sensitive device and at the same time have the possibility of a visual check of the content of the item.

The information can be stored in almost unlimited combinations of conducting and non-conducting areas. The invention is not limited to the methods described below, these are only intended for illustrative purposes.

FIGS. 1.a-1.f show various ways of placing information carrying areas for holding electronically readable information on a cartridge. In FIGS. 1.a-1.d the information carrying areas are concentrated to one axial end of the cartridge, preferably near the lid, whereas in FIGS. 1.e-1.f the information carrying areas are concentrated to a limited radial sector of the cartridge, but extending along the full length of the cartridge. The limitation is only for better illustration, the information area could put on the entire surface.

FIGS. 1.a-1.d show a cartridge 10 with an axis of rotational symmetry 11 and information carrying areas located at one axial end of the cartridge.

FIG. 1.a shows two information carrying areas 101, 102 positioned side by side in a radial direction on the surface of the cartridge (i.e. along the periphery perpendicular to the axis of symmetry). Each information carrying area covers only a limited radial sector of the surface.

FIG. 1.b shows two information carrying areas 103, 104 positioned side by side in the axial direction on the surface of the cartridge (i.e. along the periphery parallel to the axis of symmetry). Each information carrying area covers only a limited radial sector of the surface.

FIG. 1.c shows two information carrying areas 105, 106 positioned side by side in the axial direction on the surface of the cartridge (i.e. along the periphery parallel to the axis of symmetry). Each information carrying area encircles the entire radial periphery of the cartridge.

In each of FIGS. 1.a-1.c, two information carrying areas are shown side by side. There might as well, however, be several information carrying areas located side by side in axial or radial direction.

FIG. 1.d shows information carrying areas 110, 111, 112, 113, 114 positioned side by side, evenly distributed in a radial direction on the surface of the cartridge (i.e. along the periphery perpendicular to the axis of symmetry). Each information carrying area covers only a limited radial sector of the surface. Information carrying areas 110, 111, 112, 113, 114 plus identical ones situated on the hidden part of the surface are evenly distributed on the surface of the cartridge in a radial direction, i.e. extending along the whole periphery encircling the axial direction of the cartridge.

FIGS. 1.e-1.f show a cartridge 10 with an axis of rotational symmetry 11 and information carrying areas concentrated to an area 120 corresponding to a limited radial sector 121 of the cartridge 10.

FIG. 1.e shows information carrying areas 115 and 116 side by side in axial direction and extending along the major part of the axial length of the cartridge. The information carrying areas are located within a surface area 120 corresponding to a radial sector 121.

FIG. 1.f shows information carrying areas 117 and 118 side by side in radial direction and extending along the major part of the axial length of the cartridge. The information carrying areas are located within a surface area 120 corresponding to a radial sector 121.

In FIGS. 1.e and 1.f, two information carrying areas are shown within the surface area 120. There might as well, however, be several information carrying areas located side by side in axial or radial direction.

FIGS. 2.a-2.e show various ways of laying out the electrically conducting and electrically insulating areas in predefined positions within an information carrying area, implementing a binary representation of an item of information in its true and inverted form.

In each of FIGS. 2.a-2.e two information carrying areas containing an item of information in a true and inverted binary form, respectively, are schematically shown. Each information carrying area has a rectangular shape defining a longitudinal direction as the direction defined by its longest side. A direction is also defined by the direction perpendicular to the face between two neighboring predefined positions each containing a specific bit of information.

FIG. 2.a shows an embodiment with two information carrying areas 20, 21 located side by side in a direction perpendicular to the direction 205 defined by adjacent predefined positions. Each individual bit of information is implemented as a patch of electrically conducting 211 (no filling) or electrically insulating 201 (hatched) material located at a specific predefined position of the information carrying area. Neighboring patches abut each other. The structure of information carrying areas 20, 21 may e.g. be used in FIGS. 1.a, 1.d, and 1.f.

FIG. 2.b shows an embodiment with two information carrying areas 22, 23 located side by side in a direction perpendicular to the direction 225 defined by adjacent predefined positions. Each individual bit of information is implemented as a patch of electrically conducting 231 (no filling) or electrically insulating 221 (hatched) material located at a specific predefined position of the information carrying area. Neighboring patches are separated by an 'empty' space 220, 230 of width equal to the width of each of the information carrying patches 221, 231. The 'empty' space may consist of an electrically conducting or insulating layer (as long as the pads on the PCB (cf. 763, 764 on FIG. 7) are correspondingly laid out). The structure of information carrying areas 22, 23 may e.g. be used in FIGS. 1.a, 1.d, and 1.f.

FIG. 2.c shows an embodiment with two information carrying areas 24, 25 located side by side in a direction 245 defined by adjacent predefined positions. Each individual bit of information is implemented as a patch of electrically conducting 251 (no filling) or electrically insulating 241 (hatched) material located at a specific predefined position of the information carrying area. Neighboring patches abut each other. The structure of information carrying areas 24, 25 may e.g. be used in FIGS. 1.a, 1.d, and 1.f.

FIG. 2.d shows an embodiment with two information carrying areas 26, 27 located side by side in a direction 265 defined by adjacent predefined positions. Each individual bit of information is implemented as a patch of electrically conducting 262, 271 (no filling) or electrically insulating 261, 272 (hatched) material located at a specific predefined position of the information carrying area. Neighboring patches abut each other. The structure of information carrying areas 26, 27 may e.g. be used in FIGS. 1.b, 1.c, and 1.e.

FIG. 2.e shows an embodiment with two information carrying areas 28, 29 located side by side in a direction perpendicular to the direction 285 defined by adjacent predefined positions. Each individual bit of information is implemented as a patch of electrically conducting 291 (no filling) or electrically insulating 281 (hatched) material located at a specific predefined position of the information carrying area. Neighboring patches abut each other. The structure of information carrying areas 28, 29 may e.g. be used in FIGS. 1.b, 1.c, and 1.e.

FIGS. 3.a and 3.b show labels according to the invention with a multitude of information carrying areas containing electrically conducting and electrically insulating areas in predefined positions.

FIG. 3.a shows a self-adhesive label 30 consisting of a carrier foil 31 provided with information carrying areas 310, 320, 330, 340, 350, 360, 370, each containing an item of information in its binary true or inverted form. Each information carrying area consists of a rectangular electrically conducting base, to which layers of electrically insulating rectangular patches (hatched) 312, 332, 352, 372 are added in predefined positions. The true and inverted forms appear alternatingly along the radial direction of the carrier. The binary representation of the information-in information carrying area 340 is, for example, the inverse of that in 350 as indicated by corresponding bits 342 and 352, respectively, being each others inverse (342 is illustrated with no filling, indicating an electrically conducting patch, and 352 is hatched, indicating an electrically insulating patch). One predefined position 311, 321, 331, 341, 351, 361, 371 in each information carrying area 310, 320, 330, 340, 350, 360, 370, respectively, is reserved for applying a power supply voltage.

FIG. 3.b shows a preferred embodiment of a self-adhesive label 35 consisting of an electrically conducting carrier foil 36 provided with information carrying areas 315, 325, 335, 345, 355, 365, 375, each containing an item of information in its binary true or inverted form. Each information carrying area consists of patterns of rectangular patches of electrically conducting 357, 366 (no filling) and electrically insulating patches 356, 367 (hatched) added in predefined positions. All predefined positions are illustrated for areas 355 and 365, where each electrically conducting patch (being just a predefined 'empty' position on the electrically conducting foil) is indicated by a dotted boundary line. For the other information carrying areas, only the electrically insulating patches are specifically indicated. The true and inverted forms appear alternatingly along the radial direction of the carrier. The binary representation of the information in information carrying area 355 is, for example, the inverse of that in 365 as indicated by corresponding bits (356, 366) and (357, 367), respectively, being each others inverse. A predefined area 37 of the foil is reserved for applying a power supply voltage.

FIG. 4 shows a cartridge with a label containing an electronically readable information and a support for supporting the cartridge and for transferring the information from the cartridge to an electronic circuit.

FIG. 4 shows a replaceable cartridge 40 for a pen-type injection device. The cartridge has a rotational symmetry 43. A label 41 is shown before its positioning on the surface at one axial end of the cartridge. The label consists of a self-adhesive carrier 42 with information carrying areas 410, 411, 412, 413, 414, 415, each consisting of a stripe of electrically conducting foil 4151 (light grey) with electrically insulating patches 4152 (dark grey) in predefined positions, cf. FIG. 2.b and FIG. 3.a.

FIG. 4 also shows a cross sectional view of a support 46 for receiving the cartridge corresponding to a cross section of the cartridge perpendicular to the axis of symmetry and a top view of the receiving surface 45 of the support 46 corresponding to an axial direction of the cartridge. The support 46 consists of two electrically connecting supports 461, 462 separated by an electrically insulating volume 463. The electrically connecting supports 461, 462 consist of alternating layers of electrically conducting and electrically insulating silicone rubber as shown in the 'top view' illustration by identical areas 451 and 452. The areas that are designed to receive the predefined positions 4152 (comprising an electrically insulating or conducting layer) of the information carrying areas on the cartridge are indicated by a dark grey filling, e.g. 454, 457, whereas areas with no filling, e.g. 455, 466, correspond to 'empty space' between predefined positions containing an information bit (cf. 230 in FIG. 2.*b*). The geometry of the insulating area 453, corresponding to a 'top view' cross section of insulating volume 463, is designed to match the geometry of the information carrying areas on the cartridge in such a way that two adjacent information carrying areas may be received by the support independently of the radial orientation of the cartridge, when placed in the support, cf. the discussion in connection with FIG. 6 below.

FIGS. 5.*a*-5.*c* show various geometries of an electrically connecting support according to the invention.

Common for FIGS. 5.*a*-5.*c* is that the layer thicknesses are exaggerated compared to the dimensions of the patches 51 on the information carrying areas and the pads 52 on the PCB.

FIG. 5.*a* shows an embodiment of an electrically connecting support 50, where the thickness $T_{il}$ 530 of the insulating layer 53 is larger than the thickness $T_{cl}$ 540 of the conducting layer 54. The patches 51 of the information carrying area are shown to be of equal width Wpda 510 and to abut each other. The pads 52 on the PCB are shown to have equal width Wcp 520 and to be evenly distributed with a distance Diacp 521 between each pad.

FIG. 5.*b* shows an embodiment of an electrically connecting support 50, where the thickness $T_{il}$ of the insulating layer 53 is smaller than the thickness $T_{cl}$ of the conducting layer 54.

FIG. 5.*c* shows an embodiment of an electrically connecting support 50, where the thickness $T_{il}$ of the insulating layer 53 equals the thickness $T_{cl}$ of the conducting layer 54.

The relation Diacp>2*$T_{cl}$ makes sure that the electrical states of adjacent information carrying patches on the cartridge are not transferred to the same pad in the contact area under the assumption that the border between adjacent patches is located at a position 'corresponding to midway between two pads'. The fulfillment of the relation Wcp>$T_{il}$+$T_{cl}$ ensures that at least one conducting layer contacts any given pad. Correspondingly, the fulfillment of the relation Wpda>$T_{il}$+$T_{cl}$ ensures that each patch has contact to at least one of the conducting layers of an electrically connecting support, when the cartridge is properly placed in the support.

In FIGS. 5.*a*-5.*c*, the information carrying patches on the cartridge are shown as abutted. This need not be the case, however. They may have any width Wpda as long as the relation Wpda>$T_{il}$+$T_{cl}$ is fulfilled to ensure that at least one conducting layer contacts any given information carrying patch.

The relations reflect the minimum distances of pads and patches and between pads and thus for given layer thicknesses determine the information density (minimum width per bit).

Figure 6:
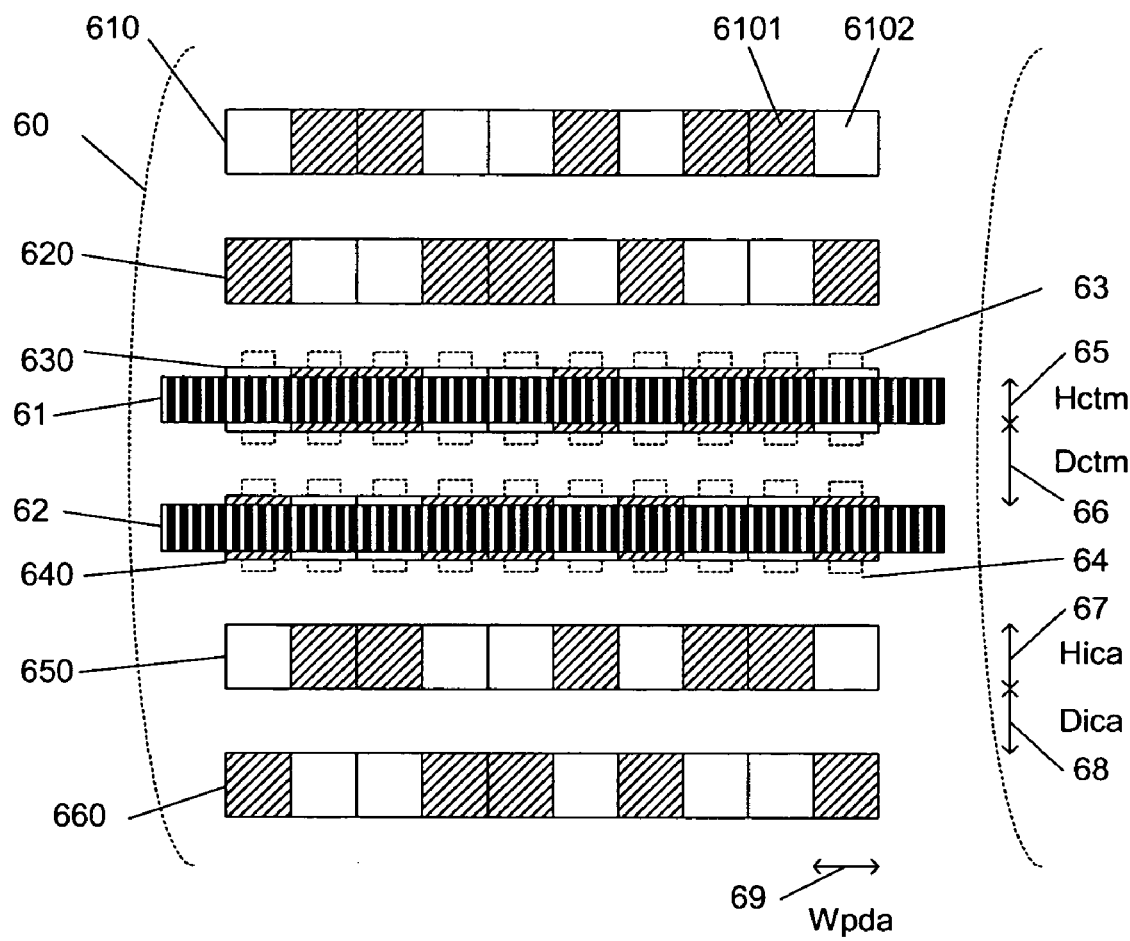
FIG. 6 shows geometries involved in reading an item of information provided a multitude of times along the periphery of a cartridge with a rotational symmetry by means of two electrically connecting supports.

FIG. 6 shows geometries involved in reading an item of information provided a multitude of times along the periphery of a cartridge with a rotational symmetry by means of two electrically connecting supports.

In FIG. 6, the electrically connecting supports 61, 62 are shown in a position where they read information from information carrying areas 630, 640, respectively, and transfer the information to groups of pads 63, 64, respectively, on a PCB. The information carrying areas 610, 620, 630, 640, 650, 660 on a label 60 carry an item of information alternatingly in a binary true and inverted form as indicated by the schematically shown individual patches of equal width Wpda 69. The patches are either electrically conducting 6102 (no filling) or electrically insulating 6101 (hatched).

The following geometric relations between the information carrying areas positioned on a cartridge and the electrically connecting supports 61, 62 of a support according to the invention for the cartridge are preferred:

Hica<Dctm<2*Hica+Dica, and
Hctm<Dica<2*Hctm+Dctm, where
Hica=Height 67 of information carrying areas
Dica=Distance 68 between information carrying areas
Hctm=Height 65 of electrically connecting supports
Dctm=Distance 66 between electrically connecting supports.

Hica<Dctm ensures that the cartridge cannot be positioned in such a way that a given information carrying area has contact to two electrically connecting supports at the same time.

Hctm<Dica ensures that the cartridge cannot be positioned in such a way that a given electrically connecting support has contact to two information carrying areas at the same time.

Dica<2*Hctm+Dctm ensures that the cartridge cannot be positioned in such a way that the electrically connecting supports fall entirely between two information carrying areas, in which case they would not have contact to any of the information carrying areas of the cartridge.

Dctm<2*Hica+Dica ensures that the cartridge cannot be positioned in such a way that two adjacent information carrying areas fall entirely between the electrically connecting supports, in which case the latter might not have contact to any of the information carrying areas of the cartridge.

In a preferred embodiment, the following relation is fulfilled (in addition to the above mentioned relations between Dctm, Hctm, Dica, Hica), Dctm+Hctm=Dica+Hica, which ensures that the electrically connecting supports 61, 62 will have contact to two of the information carrying areas irrespective of the radial orientation of the cartridge in the support.

Figure 7:
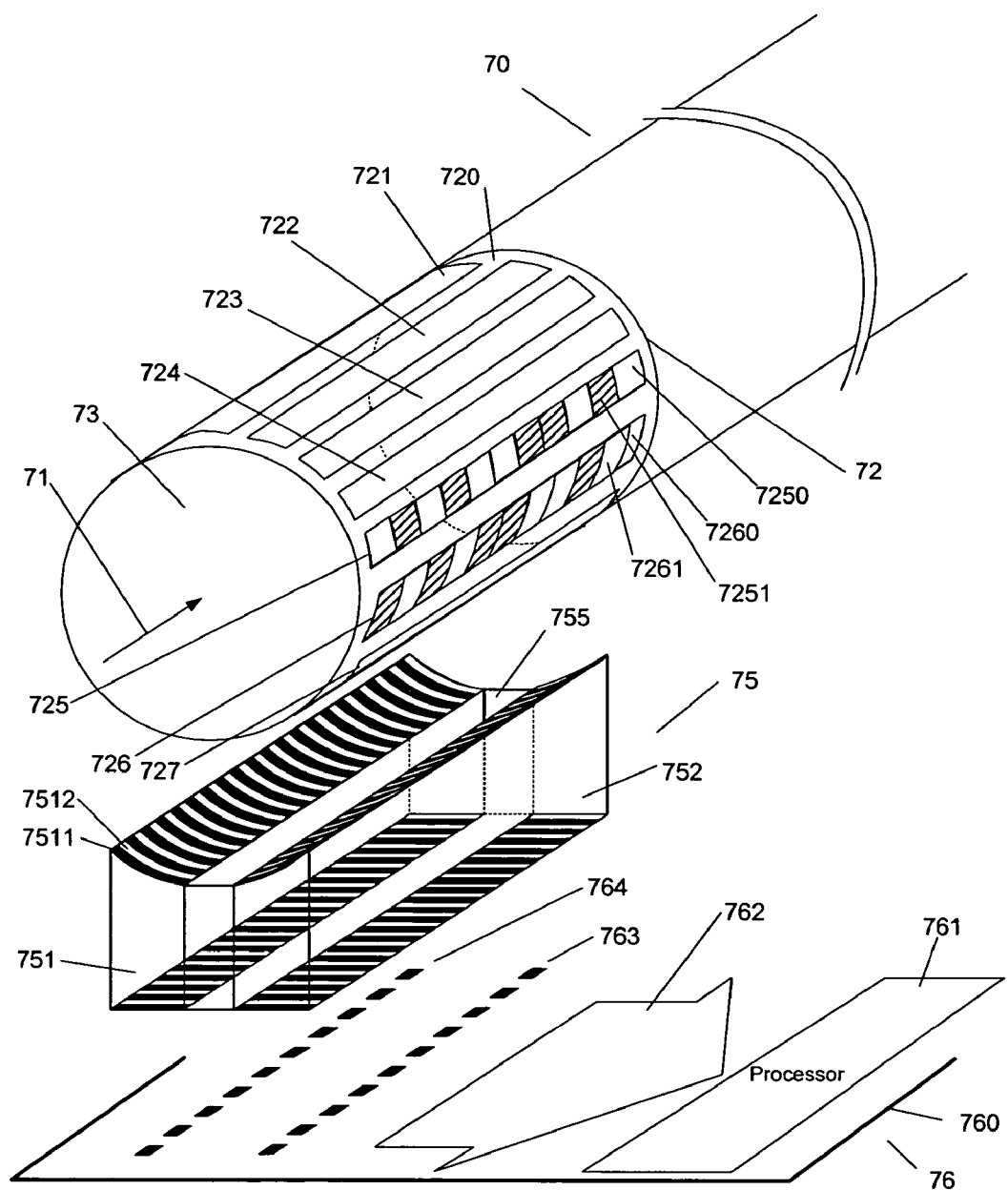
FIG. 7 shows a cartridge containing an electrically readable information according to the invention in the form of patterns of patches in the axial direction of the cartridge and a support comprising two electrically connecting supports for transferring the information to an electronic circuit, and FIGS. 8.a-8.b show an example of a cartridge and a support according to the invention comprising three electrically connecting supports made of elastic materials.

FIG. 7 shows a cartridge containing an electrically readable information according to the invention in the form of patterns of patches in the axial direction of the cartridge and a support comprising two electrically connecting supports for transferring the information to an electronic circuit.

A support according to the invention has the combined function of receiving and mechanically supporting a part of the cartridge provided with information carrying areas AND of transferring the information from these information carrying areas to an electronic circuit for further processing.

In FIG. 7, the cartridge 70 is only partially shown, as indicated by the 'broken' outline in the right-hand part of the cartridge. The cartridge possesses a rotational symmetry as indicated by the arrow 71 symbolizing the axis of symmetry. A label 72 containing information carrying areas laid out in the axial direction of the cartridge, is located on the outer surface at one axial end of the cartridge, where a lid 73, optionally in the form of a piston (e.g. when the cartridge is a replaceable medication cartridge for a medication delivery device), provides a closure of the cartridge.

The label 72 comprises an electrically conducting foil 720 having information carrying areas 721-727 extending in the axial direction of the cartridge. In FIG. 7, a multitude of information carrying areas (721-727 plus the ones situated on the hidden part of the surface) are evenly distributed on the surface of the cartridge in a radial direction (i.e. along the whole periphery encircling the axial direction of the cartridge). Each information carrying area, comprising patterns of electrically conducting 7250, 7260, 7261 and electrically insulating 7251 patches, thus only covers a limited radial sector of the surface. In the embodiment of FIG. 7, the electrically conducting 'end'-patches 7250, 7260 may be used for connecting a power supply voltage.

Each of the information carrying areas contain an item of information in the form of patterns of electrically conducting and electrically insulating areas. Each pattern represents an item of information in binary form. Each bit of information is represented by an electrically characteristic layer in a predefined position in the information carrying area. A binary one in a specific predefined position may be represented by an electrically conducting layer covering that predefined position, and a binary zero in a specific predefined position may be represented by an electrically insulating layer covering that predefined position. Alternatively, binary one may be represented by an insulating layer and binary zero by a conducting layer.

Because the foil 720 containing the information carrying areas is electrically conducting, it is only necessary to apply an electrically insulating layer (e.g. a paint) to the predefined positions representing one of the a binary states (in this embodiment 'zero').

In FIG. 7, the cartridge is shown in a position just above the support 75, which, again for illustrative purposes, is shown just above a PCB with electronic components and connecting wires 76 containing pads 763, 764 with electrical connections, symbolically indicated by an arrow 762, to a processing unit 761, e.g. a microprocessor. The support consists of one or more electrically connecting supports 751, 752 embedded in an electrically insulating material 755. The electrically connecting supports comprise alternating layers of electrically conducting 7511 and electrically insulating 7512 layers of an elastomeric material, e.g. silicone rubber with the electrically conducting layer having a concentration of carbon black sufficient for electrical conduction. Each electrically conducting layer is electrically insulated from all other electrically conducting layers, so that each electrically conducting layer in effect represents an insulated conductor. By controlling the layer thicknesses, the maximum 'density of information' in the axial direction may be controlled.

In the embodiments of FIG. 7, the support, including the electrically connecting supports, is shown to be adapted to receive the curved shape of the part of the cartridge, where the information carrying areas are located, by shaping them equivalently. This makes possible the use of non-elastic materials for the support, if convenient.

In an operating configuration, the support is placed (and optionally fastened) on the PCB 760 so that electrical contact between the electrically connecting supports 751, 752 and the pads 763, 764 is ensured. The cartridge is positioned on the support so that electrical contact between two of the information carrying areas in their full axial lengths (i.e. involving all patches of a given information carrying area representing bits of information) and the electrically connecting supports is ensured. The geometrical dimensions of the patches, layers and pads and mutual distance between adjacent information carrying areas on the cartridge and corresponding electrically connecting supports are discussed above with reference to FIGS. 5 and 6.

By applying a specific electric potential to the electrically conducting foil, this potential will be transferred from those predefined areas containing a conductive layer (i.e. in the present embodiment those predefined areas not being covered by an insulating layer) to the corresponding pads on the PCB. Via the connecting circuitry, a direct measure of the pattern of binary states of the information carrying area connected to the pads by a given electrically connecting support is presented on the inputs of the processing unit, possibly by appropriately terminating the inputs with pull-up or pull-down circuitry depending on the potential applied to the electrically conducting foil and the definition of the binary states. A specific part of the foil may be preferably reserved to the application of the electric potential (e.g. an area of the foil circumfering the cartridge and not occupied by information carrying areas, in FIG. 7 e.g. the part of the foil 720 not covered by information bits in predefined positions 721-730).

The support is only shown as having an axial length corresponding to the axial length of the corresponding information carrying areas (e.g. 725 in FIG. 7) but it may of course extend in both axial directions if appropriate for the application in question. Likewise the support is shown to cover a certain radial sector (less than 90 degrees), but it may of course cover any radial sector, including 360 degrees, if appropriate. In a preferred embodiment, the sector covered by the support is less than 180 degrees allowing a direct 'vertical' placement of the cartridge in the support (in opposition to the case of a 360 degrees support, where the cartridge has to be axially inserted).

In FIG. 7, the label containing information carrying areas is placed in one axial end of the cartridge covering only the space occupied by the axial extent of the lid/piston to ensure that a full view of the contents of the cartridge is available for inspection. Of course it might be located in any convenient position along the surface of the cartridge. Similarly, in FIG. 7, the information carrying areas extend in the axial direction of the cartridge. They might as well extend in a radial direction (as discussed in connection with FIGS. 1 and 2) or in a direction there between (e.g. forming one or more helixes on the surface of the cartridge), if convenient, as long as the support, including the electrically connecting supports, is adapted thereto.

The electrical connections, schematically indicated by an arrow 762, connecting the pads 763, 764 with the processing unit 761 may be a one to one parallel set of electrical connections between each pad and a corresponding input on the processor, but it may also comprise a multiplexing or coding unit to reduce the number of necessary inputs to the processing unit.

In the embodiment in FIG. 7, the support 75 comprises two electrically connecting supports 751, 752 for simultaneously reading two items of information from two information carrying areas on the cartridge. In FIG. 7 the evenly distributed information carrying areas 721-730 contain an item of information in a true binary form alternating with the information in its inverted form as indicated by the schematically illustrated patterns of electrically conducting and insulating patches in information carrying areas 725 and 726, respectively, one pattern being the inverse of the other.

The rotational symmetry of the cartridge has the benefit that it only requires the user to position the cartridge properly in a radial direction (possibly involving a slight rotation of the cartridge around its axis of symmetry) to ensure that an electrical contact between one of the information carrying areas and the electrically connecting support is present (since the positioning in an axial direction may be mechanically ensured by the receiving means for the cartridge). The control of the cartridge being correctly positioned may be in the hands of the processing unit, which, if necessary, may indicate to the user via a display or a voice interface that a corrective action is required, and which may block further use of the device, if the cartridge is not correctly positioned.

The embodiment of FIG. 7 has the further advantage of reading the information in a binary true and inverted form, which allows the safety in reading to be improved. Instead of providing the information in its true and inverted forms, the same binary representation of the item of information may be provided in all information carrying areas and read twice, which also allows an improved safety in reading.

FIG. 8.*a*-8.*b* show an example of a cartridge and a support according to the invention comprising three electrically connecting supports made of elastic materials.

FIG. 8.*a* shows a cartridge 81 having an axis of rotational symmetry 82 being positioned just above a support 80 comprising three individual electrically connecting supports 801, 802, 803 ready for receiving the cartridge. The cartridge is provided with information carrying areas positioned on the cartridge along its radial periphery with a spacing corresponding to the geometry of the electrically connecting supports. The space between the electrically connecting supports may be filled with an insulating material (e.g. silicone rubber), not shown.

In FIG. 8.*b* the cartridge 81 is positioned in the support 80 and fixed with a slight downwards pressure indicated by the arrow 83. The support including the electrically connecting supports is made of elastic materials so that it conforms to the shape of the cartridge over the length of the support, when the cartridge is placed in the support.

The three items of information that may be simultaneously read may be identical, in which case the redundancy may be used to improve the safety in reading (by a simple majority test or by more advanced error correcting techniques).

Optionally a different coding method can be used to store the desired information. In this method the information is stored in a matrix of conductors which by a galvanic method can be translated to a binary code.

Optionally the information carrying matrix can be repeated in order to provide the information redundantly, preferably the repeating times is a whole number but not limited to this. By repeating the matrix it is ensured that only a part of the container, cartridge or carpule needs to be in contact with the sensing array.

In a preferred embodiment the matrix or repeated number of matrixes is aligned at a predetermined distance from a terminal surface of container, cartridge or carpule.

Figure 15:
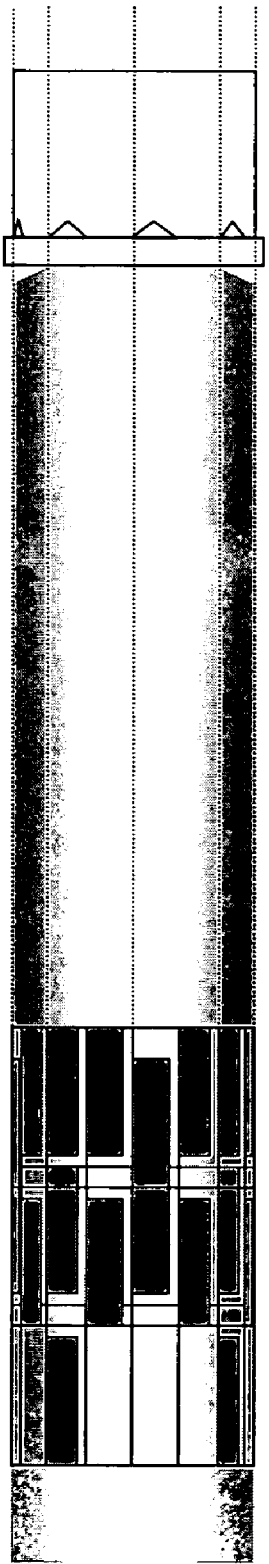
FIG. 15 shows a cartridge with an alignment means that is aligned with the conductive patterns.

Optionally the matrix contains an element designating the starting position for the coding. In an alternative embodiment, which can be used in any coding method, the container, cartridge or carpule is provided with means to ensure a certain orientation of the item. These means can optionally be in form of a code top as shown in FIG. 15. The matrix can then be put in a predefined position relative to the orientation of the container, cartridge or carpule. The means for orientating the item can be used alone or in combination with the previously mentioned alignment of the matrix in a predetermined distance from a terminal surface.

The information carrying matrix is composed to elements of a predetermined size. Each element of the matrix can contain a conducting part, a non-conducting part or both. The elements may optionally overlap each other. By adjusting the dimensions of the sensing equipment to the dimensions of the elements composing the matrix it can be assured that the conductors have at least one contact point to the sensors and that an optionally applied conduction band only touches the desired conductors.

The information stored in the matrix can be increased by increasing the matrix. Hereby it is possible to repeat the information and hereby diminish possible reading errors or simply have more information stored in the matrix. By increasing the number of cells in the width of the matrix the system of notation can be increased from binary to triary and so on. By increasing the number of cells in the height of the matrix the amount digits can be increased.

Some preferred embodiments have been shown in the foregoing, but it should be stressed that the invention is not limited to these, but may be embodied in other ways within the subject-matter defined in the following claims.

EXAMPLE 1

One way to carry out the marking of the cartridges is described in the following. A printing facility receives clear, transparent polyester foil delivered in rolls from a supplier. The polyester is delivered with clear adhesive and a protective paper carrier applied on the backside of the polyester foil. The adhesive is strongly attached to the polyester and is weakly attached to the carrier paper. This makes it possible to separate the polyester with the attached adhesive from the carrier paper and later to apply and attach the polyester to the surface of a product. In one process line the written information and the conductive polymer are applied on the frontside of the polyester foil by a suitable printing technique such as screen printing or rotaflex printing. Also, the roll of polyester is cut into separate labels by knife tools that only penetrate and cut the polyester but not the carrier paper. These finished adhesive labels on a carrier paper roll are obtained. The text is printed with conventional printing pastes. The conductive, transparent polymer is obtained from for example AGFA-GEVAERT in Belgium that delivers printing paste formulations under the trademark ORGACON. The rolls are then transferred to a labelling facility that applies the labels on glass cartridges. The glass cartridges have been filled with drug prior to the labelling.

EXAMPLE 2

A printing facility produces a roll of labels with text printed onto it and with adhesive and carrier paper on the backside. This roll is referred to as the first roll. The first roll is equivalent to example one, however the conductive structures have not been applied on it. The front side of a second roll of clear polyester is covered entirely with indium tin oxide (ITO) in a suitable plasma coating facility, for example as found at Fraunhofer Institut for Electronenstrahl und Plasmatechnik, Dresden, Germany. The second roll is structured by means of aqueous etching as it is known from manufacturing of flexible electronic wireboards, as produced by Mekoprint, Randers, Denmark and many others. The structuring is accomplished by covering the second roll by resist applied by screen printing and then leading the roll through etching processes comprising etching of the part of the indium tin oxide coating, which is not covered by resist, in a solution of hydrochloric acid and cupric chloride or another suitable acidic and oxidizing environment followed by removal of the resists by strong alkali solution. Adhesive and carrier paper is then applied to the backside of the second polyester roll. The roll is cut to individual labels by a knife tool as described in example one. Alignment of the patterning of the ITO structures and the following cutting can be accomplished by means of a series of mechanical alignment holes that penetrate the foil. These holes are cut as a part of the resist application and are later available for the alignment of the knife tool versus the roll during cutting of the labels. The first and second rolls are then transferred to the labelling facilities that firstly apply labels from the first roll on the medical cartridge, secondly apply the labels from the second roll on the medical cartridge. In this way a cartridge is obtained, where a mainly transparent label with text printed onto it is attached to the medical cartridge which is furthermore covered with a transparent label that contains conductive structures placed as the outer-most cylindrical surface of the finished cartridge product.

EXAMPLE 3

Figure 21:
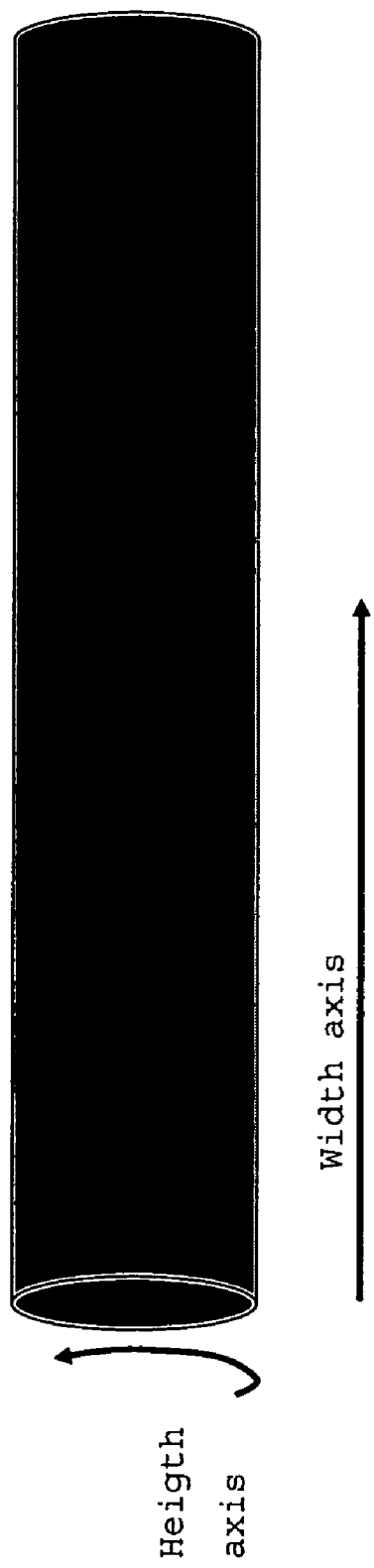
FIG. 21 shows the definition of axis.

In the following text height and vertical direction of structures on the cylindrical surface of the cartridge and the contact array refer to an axis that follows the round-going circumference of the cylinder, whereas width and horizontal directions refer to an axis that follows the cylindrical axis, as indicated on FIG. 21.

A cell on the cartridge surface is defined to have the following dimensions:

Height=1/16 of the circumference=π*11.2 mm divided by 16=2.2 mm

Width=7.5 mm

Figure 9:
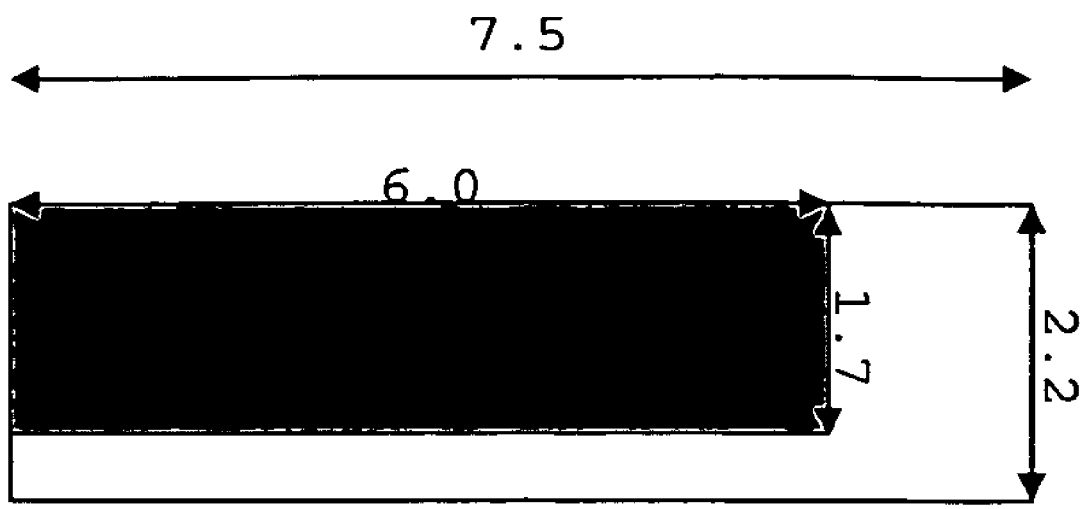
FIG. 9 shows an example of an element to the coding matrix.
Figure 10:
FIG. 10 shows an example of another element to the coding matrix.

One cell can contain one bit of information. The bit value depends on how the conductor is printed in the cell. The conductor in FIG. 9 is an example of the bit-value ONE. FIG. 10 is an example of the bit-value ZERO. Three columns of 16 cells are distributed around the circumference of the cartridge, as shown in FIG. 11. The height of the cell ensures that the lower boundary of the first cell is essentially placed at the upper boundary of the 16th cell.

Figure 12:
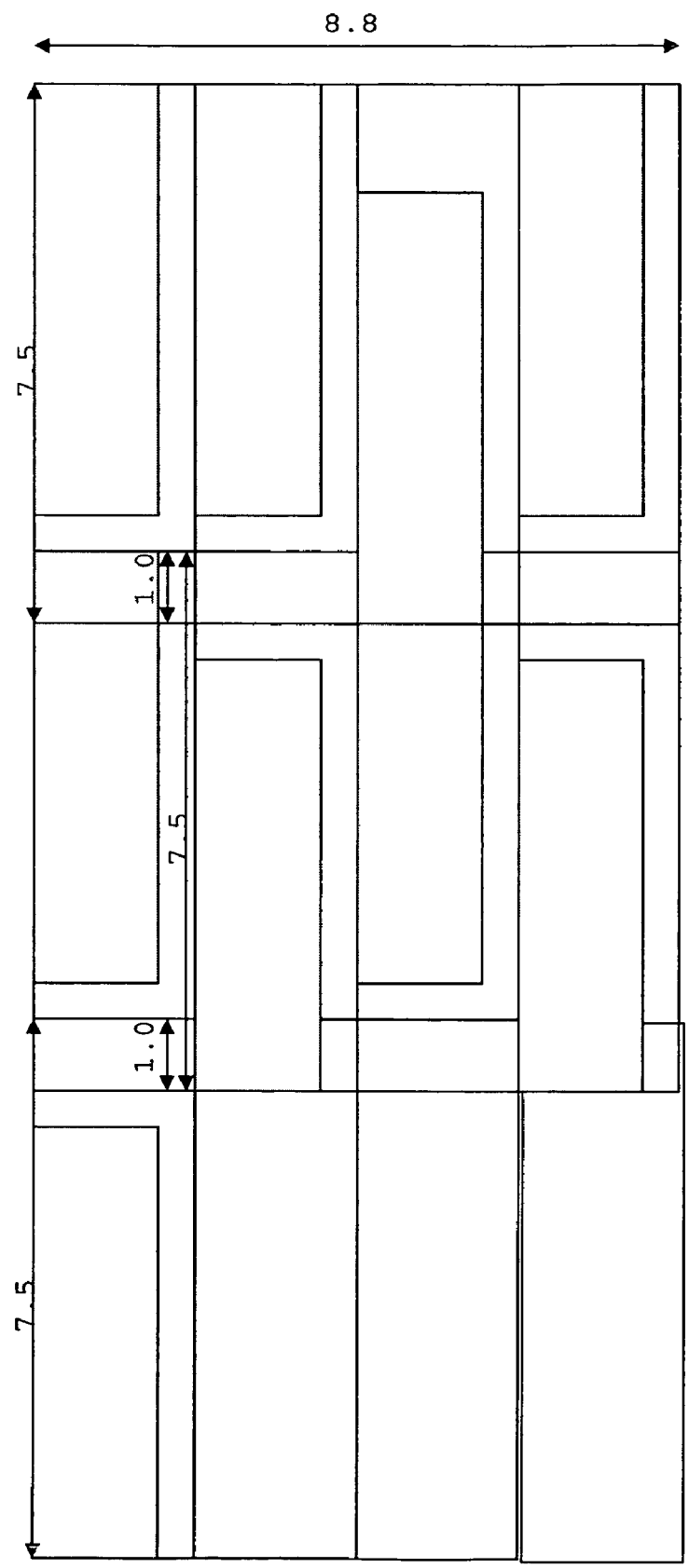
FIG. 12 shows a 4 times 3 coding matrix.

The matrix with 3 times 16 cells shown in FIG. 11 repeats the same information 4 times in vertical direction. The smallest matrix that contains all the information is 4 cells high and 3 cells wide (FIG. 12). The cells overlap each other in horizontal direction. The repetition of the information ensures that only a part of the cartridge needs to be brought into contact with the reading array to be able to read all of the encoded information content. The first column from left in FIG. 11 contains a position indication cell. Cells encoded with the value ONE in the first columns indicate the uppermost cell in the previously described 4×3 matrix. The next two columns contain 8 bits of information. The 8 bits can contain redundant information to be able to detect erroneous reading of information. By adding more columns a higher number of bits can be stored on the surface of the cartridge.

Figure 13:
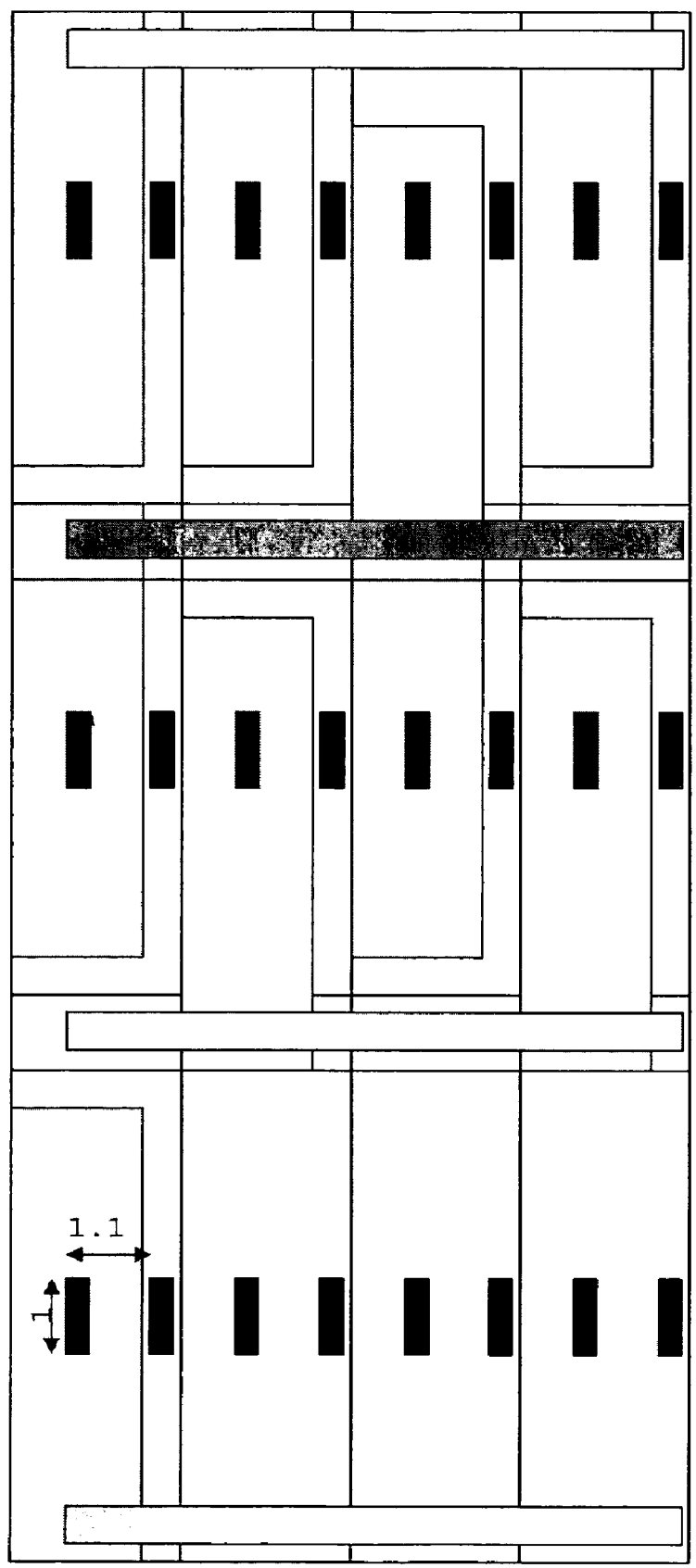
FIG. 13 shows the coupling of the conductive patterns to the contact array.
Figure 14:
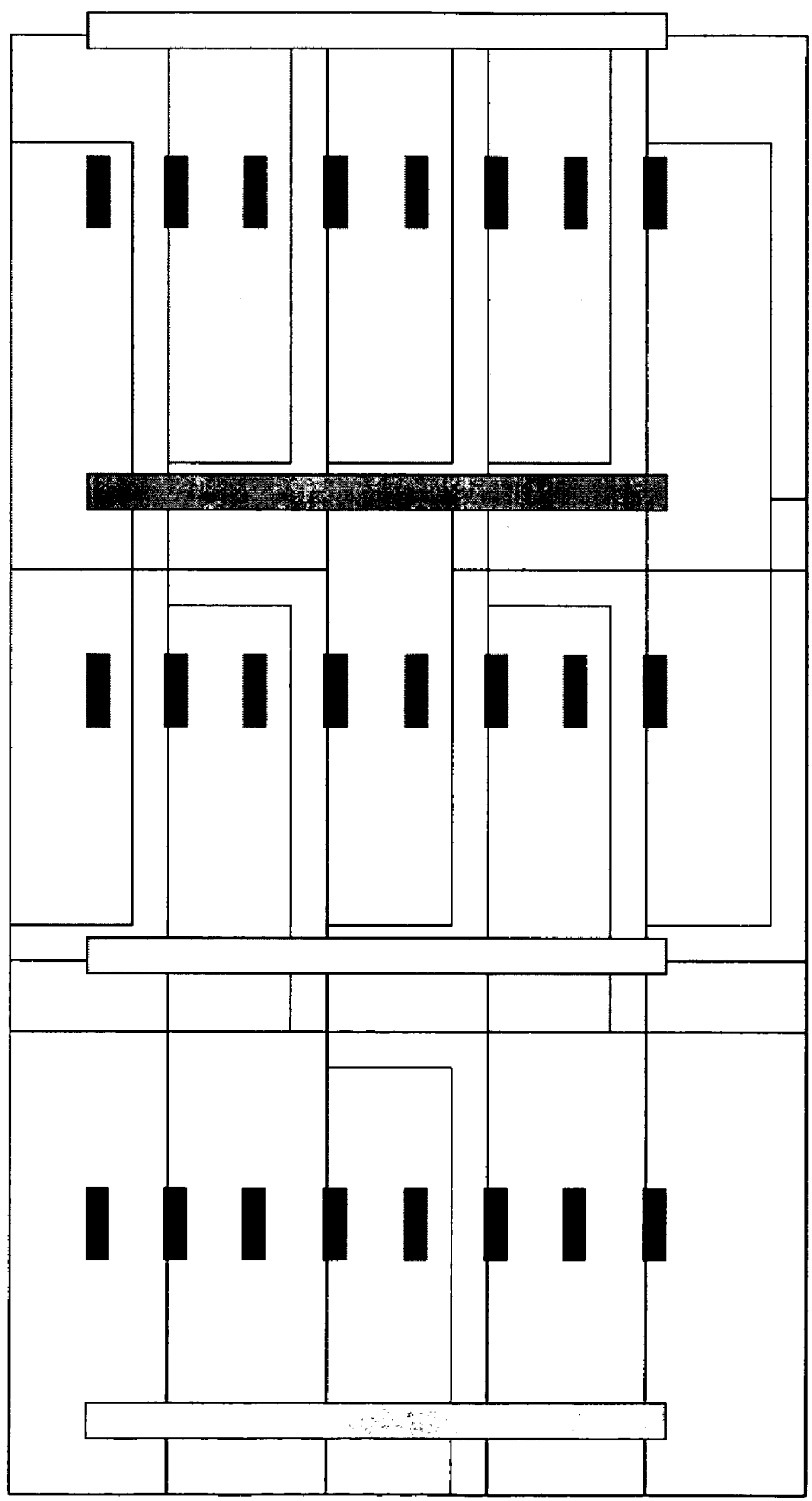
FIG. 14 shows the coupling of the conductive patterns to the contact array as in FIG. 13 where the cartridge is displaced.

FIGS. 13 and 14 show how an elastomeric contact array is coupled to the described conductive patterns. Three types of coupling areas are present on the projected elastomeric contact array. Firstly, small areas with the dimensions of 1×0,3 mm, called sensing areas, are repeated as an 8×3 matrix. Two neighboring sensing areas are vertically displaced by half of the cell height. One cell is thereby coupled to one or two sensing areas. This also applies if the cartridge is rotated versus the sensing area, as shown in FIG. 14. A sensing area height is kept sufficiently low to ensure that one sensing area can only be coupled to one cell, not two. The second and third kind of areas on the contact are called A and B conductors. (The A conductor is marked black (the two large black bars) in FIG. 13, the B conductor is dark grey (the two large dark grey bars)). The conductive area in a cell is always coupled to either an A or a B conductor. This allows us to distinguish between encoded ONEs or ZEROs in the cells. For example, in column two in FIG. 13, cells that are coupled with the B conductor are ONEs whereas cells that are coupled with the A conductor are ZEROs. To detect this, the following sequence is accomplished.

Electrical tension on A conductors is applied.

For each sensing area it is measured whether a tension is applied through the cell on the cartridge. The results are stored as reading A related to each sensing area.

Electrical tension on B conductors is then applied.

For each sensing area it is again measured whether a tension is applied through the cell on the cartridge. The results are stored as reading B related to each sensing area.

Now, the A and B readings can be used to calculate whether each sensing area is coupled to either ONES or ZEROS. In the case of the second columns in FIG. 13 we get the following rules that should be used for each sensing area.

TABLE 1

| Reading A | Reading B | Result |
|---|---|---|
| ONE | ZERO | ZERO |
| ZERO | ONE | ONE |
| ONE | ONE | Reading error |
| ZERO | ZERO | Reading error |

To transform the sensing readings to an 8 bit long information string, the position of the information mark in the first columns of FIGS. 13 and 14 needs to be detected. A sensing area related to the first columns that reads a ONE indicates the uppermost row in the information carrying matrix shown in FIG. 12. Due to the described geometrical constraint between the contact area and the conductive pattern this indicator mark can enable a conversion of the sensing readings into an 8 bit long information string independently of the rotation of the cartridge versus the contact array.

Figure 17:
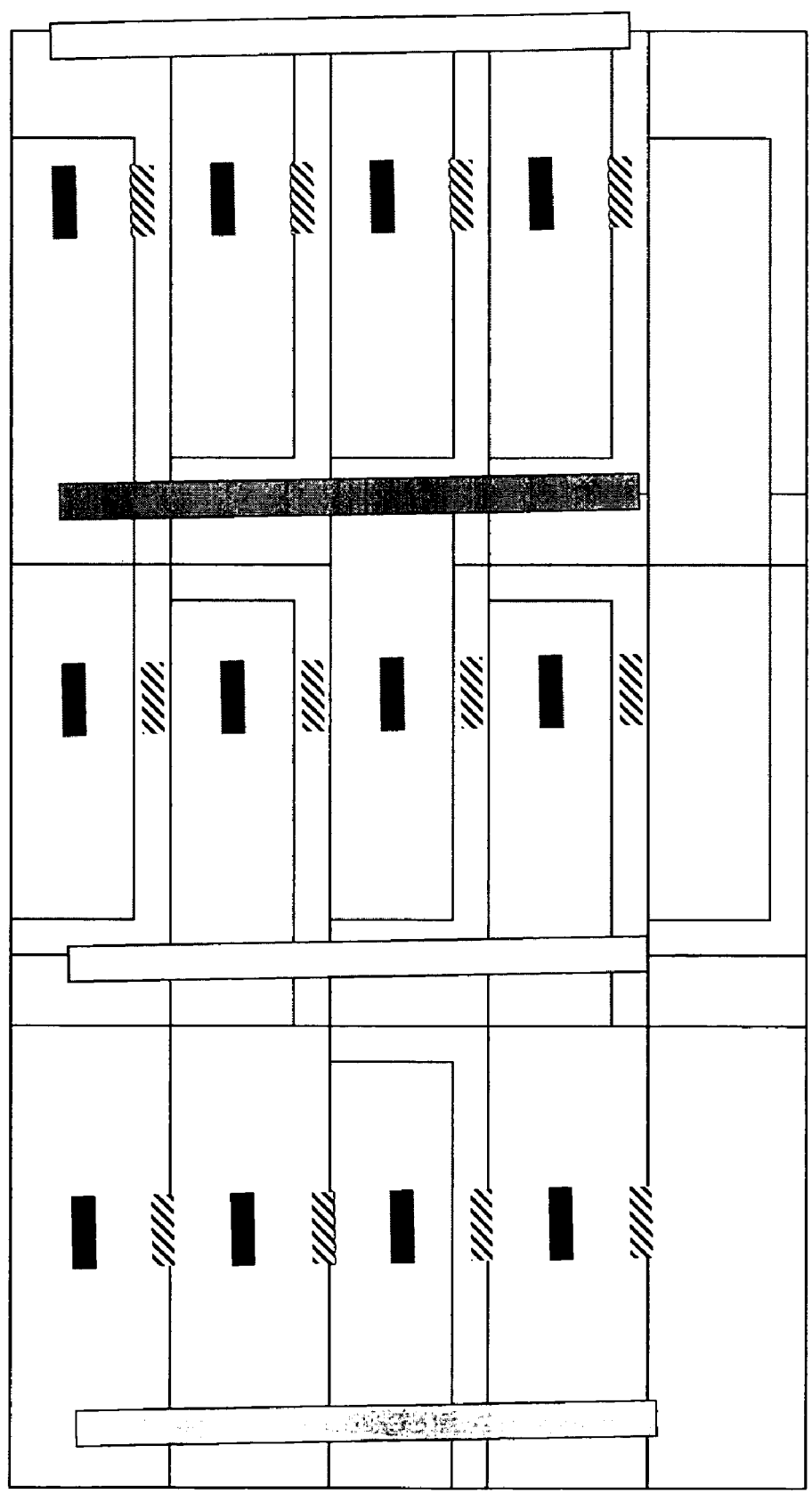
FIG. 17 shows rejection of sensing readings at or near the non-conductive rows. The sensing areas, that are hatched, are not considered in the transformation of the sensing readings to a string of information.

Table 1 describes how certain combinations of A and B readings are interpreted as erroneous readings. The ZERO-ZERO and ONE-ONE readings can be used to detect either lack of contacts or short-circuits in the contact between the contact array and the conductive patterns. This is relevant if the conductive patterns have been damaged by scratches or polluted with non-conductive matter. The occurrence of ZERO-ZERO readings can also be caused by sensing areas that are positioned in the non-conductive void between the conductive areas of two cells. The detection of such ZERO-ZERO readings can be involved an algorithm that transforms the sensing area readings to a string of bits by discarding the set of rows of sensing readings that is encumbered with a significant number of erroneous readings. FIG. 17 shows an example of rejection of every second row whereby the remaining sensing areas in column two and three are free of ZERO-ZERO reading cause by non-conductive areas voids.

EXAMPLE 4

Figure 16:
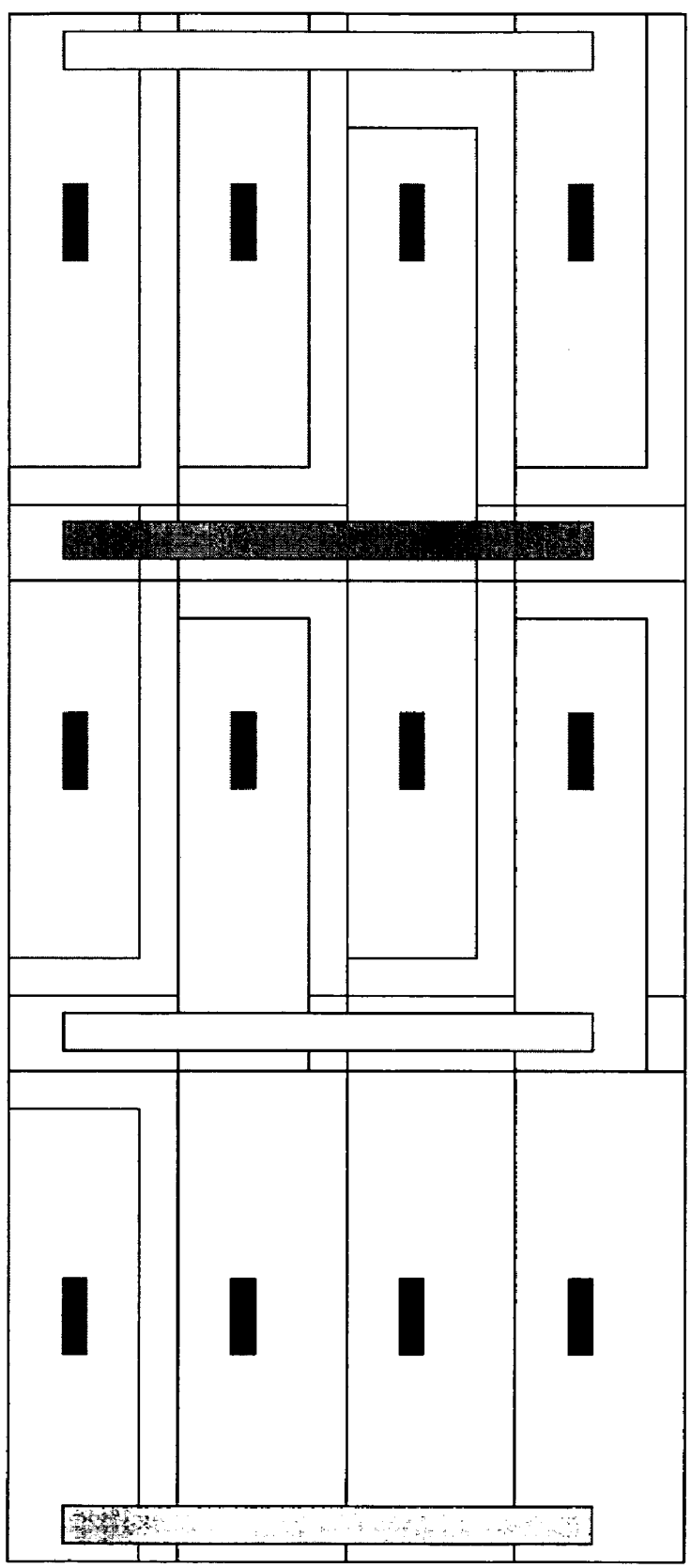
FIG. 16 shows a sensing array with a reduced number of sensing areas.

The previous example gave a method that was able to read the matrix of conductive structures independently of the rotational orientation of the cartridge. However, a structure, called a code top, placed at the end of the cartridge can restrict the allowed positions of the cartridge versus the code reader (FIG. 15). A code top is today placed on all insulin cartridges for durable devices from Novo Nordisk by means of a simple snap joint that does not hinder rotation along the cylindrical axis. The code top contains 8 mechanical wedges distributed evenly around the circumference of the cylindrical surface of the code top. If the code top is aligned with respect to the conductive patterns, as shown in FIG. 15, and then kept at that position by for example gluing the code top to the cartridge during production of cartridge, then the orientation of the cells will be correlated to the orientation of the mechanical wedges at the code top. The device that contains the reading contact array contains various means for maintaining the correct position of the cartridge, including a counterpart to the wedges. If the wedge counterpart orientation is controlled with respect to the sensing areas at the contact array, then it will be possible to restrict the allowed positions of the conductive structures with respect to sensing areas. In that case, only one sensing area per cell is needed, as shown on FIG. 16. This reduces the complexity of the sensing array.

EXAMPLE 5

Figure 18:
FIG. 18 shows a cell that encodes a ONE, FIG. 19 shoes a cell that encodes a ZERO.
Figure 19:
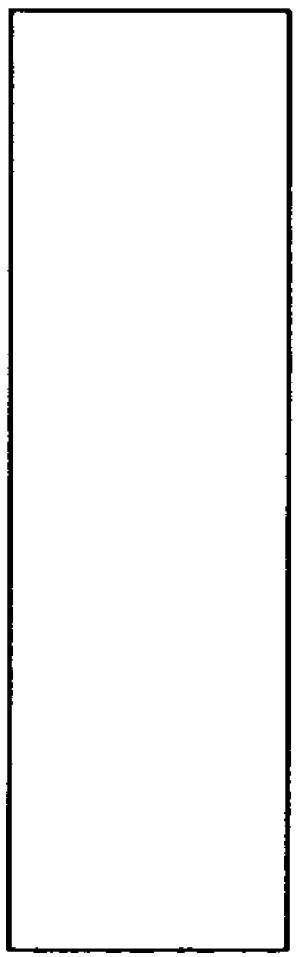
Figure 20:
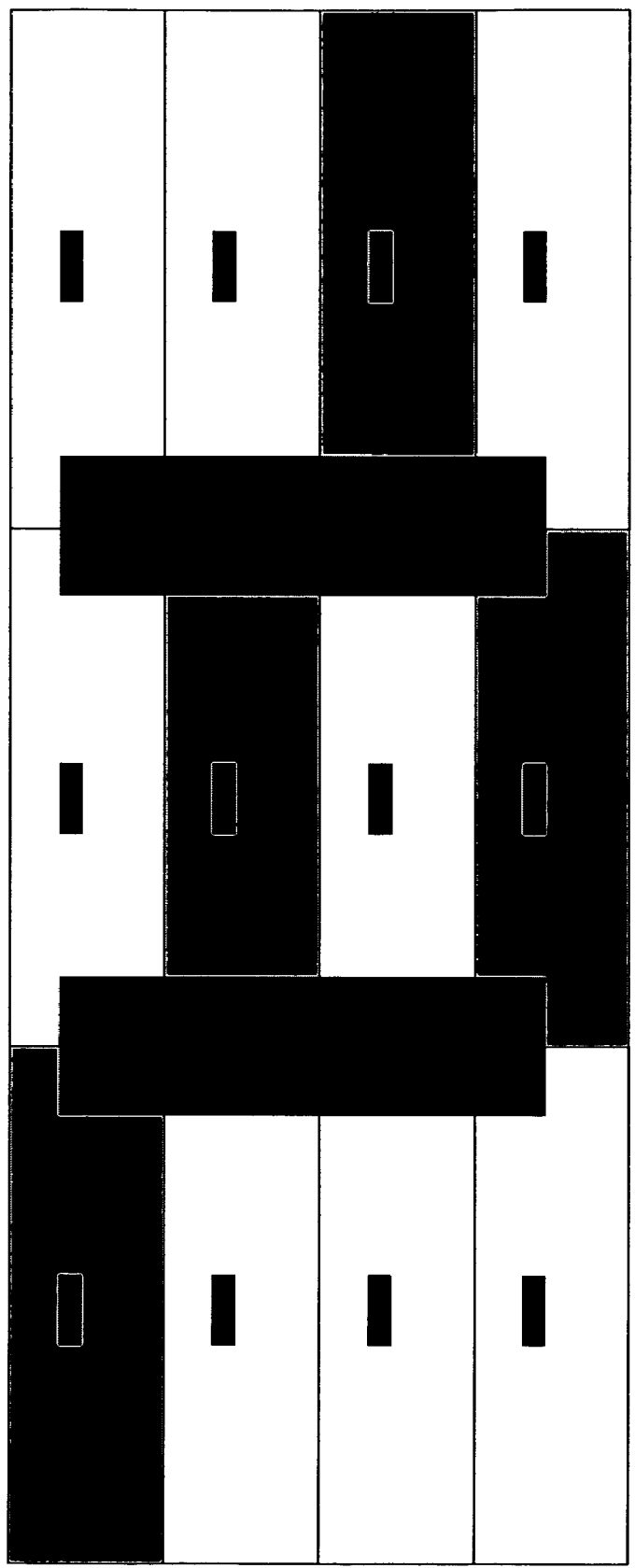
FIG. 20 shows a matrix cell with conductive areas, sensing arrays and conductors that apply electrical tension on the conductive structures.

More simple designs of cells and contact arrays that do not contain the explained A and B readings can be utilized. FIGS. 18 and 19 show cells that encode ONEs and ZEROs. FIG. 20 shows how these can be read by means of sensing areas and conductors that apply tension on the conductive areas during reading.

The invention claimed is:

1. A medication container for holding a medicament, the container comprising:
an electronically readable item of information provided as an electrically conductive pattern defined by electrically insulating and electrically conducting areas in the form of a code, wherein the electrically conducting areas are formed by a transparent conductor,
and wherein the medication container is structured for use in treatment of a patient.

2. A medication container according to claim 1 wherein the container is a cartridge.

3. The medication container according to claim 1, wherein the item of information is redundantly provided at least twice in areas corresponding to the relevant state of each bit of information in predefined positions on a surface of the container.

4. The medication container according to claim 1, wherein said item of information is formed on a self-adhesive carrier positioned on a surface of the container.

5. The medication container according to claim 3, wherein said container has an axis of rotational symmetry.

6. The medication container according to claim 5, wherein information carrying areas containing said item of information in its true and inverted forms, respectively, are positioned side by side in the direction of said axis of symmetry of said container.

7. The medication container according to claim 6, wherein information carrying areas containing said item of information in its true and inverted forms, respectively, are positioned side by side in the direction of a circumference of said axis of symmetry of said container.

8. The medication container according to claim 7, wherein information carrying areas containing said item of information in its true and inverted forms, respectively, appear alternatingly a multitude of times in a direction of a circumference of said axis of symmetry of said container.

9. The medication container according to claim 3, wherein said item of information is provided in any of its binary forms by applying electrically insulating areas in predefined positions on the surface of an electrically conducting foil positioned on said container in such a way that an electrically insulating area is applied at those predefined positions representing one predefined binary state, and an electrically conductive area is provided at those predefined positions representing a complementary binary state.

10. The medication container according to claim 1 wherein the information is stored in a matrix.

11. The medication container according to claim 10, wherein the matrix contains a sequence designating the starting point.

12. The medication container according to claim 10, wherein the matrix is repeated.

13. The medication container according to claim 10, wherein the matrix is repeated a whole number of times.

14. The medication container according to claim 10, wherein the container has means to ensure a certain orientation of the item.

15. The medication container according to claim 10, wherein the matrix is put at a predefined distance from a terminal surface.

16. The medication container according to claim 3, wherein said item of electronically readable information is provided on the container in an optically readable form.

17. The medication container according to claim 1, wherein the transparent conductor is a polymer.

18. The medication container according to claim 17, wherein the polymer comprises poly(3,4-ethylenedioxythiophene)-polystyrenedesulphonate (PEDOT-PPS) and/or polymers with networks of bis(ethylenedioxy)tetrathiafulvene or iodine or bromine salt thereof.

19. The medication container according to claim 18, wherein the polymer comprises α-BEDO-TFF2I3, β-BEDO-TFF2I3 and/or BEDO-TFF2.4I3.

20. The medication container according claim 1, wherein the transparent conductor is one or more thin layers of Indium Tin Oxide (ITO).

21. The medication container according to claim 20, wherein one or more Indium Tin Oxide layer is mixed with one or more thin layers of silver.

22. The medication container according to claim 1, wherein the container is structured to allow visual inspection of the contents of the container.

23. A medication container label comprising an electronically readable item of information provided as an electrically conductive pattern defined by electrically insulating and electrically conducting areas in the form of a code, wherein the electrically conductive areas are formed by a transparent conductor.

24. The medication container label according to claim 23, wherein the label is transparent.

25. The medication container label according to claim 23, wherein there is text on the label.

26. The medication container label according to claim 25, wherein the transparent conductor is covering at least a part of the text.

* * * * *